US010220148B2

(12) United States Patent
Johannesson et al.

(10) Patent No.: US 10,220,148 B2
(45) Date of Patent: *Mar. 5, 2019

(54) ACTUATION MECHANISMS FOR DUAL CHAMBER MIXING SYRINGES

(71) Applicant: UNL Holdings LLC, New York, NY (US)

(72) Inventors: Robert E. Johannesson, Mechanicsburg, PA (US); Peter J. Dungar, York, PA (US); Molly M. Weaver, Norristown, PA (US); Flora Felsovalyi, Oak Ridge, NJ (US)

(73) Assignee: UNL Holdings LLC, New York, NY (US)

( * ) Notice: Subject to any disclaimer, the term of this patent is extended or adjusted under 35 U.S.C. 154(b) by 209 days.

This patent is subject to a terminal disclaimer.

(21) Appl. No.: 15/363,924

(22) Filed: Nov. 29, 2016

(65) Prior Publication Data

US 2017/0080155 A1    Mar. 23, 2017

Related U.S. Application Data

(63) Continuation of application No. 14/296,194, filed on Jun. 4, 2014, now Pat. No. 9,539,393.

(Continued)

(51) Int. Cl.
*A61M 5/20* (2006.01)
*A61M 5/315* (2006.01)
(Continued)

(52) U.S. Cl.
CPC ......... *A61M 5/2066* (2013.01); *A61M 5/284* (2013.01); *A61M 5/31596* (2013.01);
(Continued)

(58) Field of Classification Search
CPC ............... A61M 5/2066; A61M 5/284; A61M 5/31596; A61M 5/3234; A61M 2005/31598; A61M 2005/3236
See application file for complete search history.

(56) References Cited

U.S. PATENT DOCUMENTS 2,591,706 A    4/1952  Lockhart
3,066,670 A    12/1962 Stauffer
(Continued)

FOREIGN PATENT DOCUMENTS

CN    2577863 Y    10/2003
FR    2741810 A1    6/1997
(Continued)

OTHER PUBLICATIONS

Notification Concerning Transmittal of International Preliminary Report on Patentability, International Application No. PCT/US2014/040917, dated Dec. 17, 2015 (10 pgs).
(Continued)

*Primary Examiner* — Andrew Gilbert
*Assistant Examiner* — James D Ponton
(74) *Attorney, Agent, or Firm* — Hamilton, Brook, Smith & Reynolds, P.C.

(57) ABSTRACT

An automatic mixing device, an actuating device having integrated plunger and configured to be removably mounted to the automatic mixing device, and a retractable syringe having the automatic mixing device are provided. The actuating device has an initially compressed spring and a trigger member that is rotatable to initiate spring decompression to drive depression of a mixing plunger seal of the automatic mixing device. Another seal located in an outer chamber of the mixing device is capable of axial movement upon depression of the mixing plunger, from a first position in sealing engagement with one or more apertures in an inner (Continued)

barrel to a second position intermediate the apertures and vents in an outer barrel. This allows depression of the mixing plunger to force a first substance from the outer chamber through the apertures to mix with a second substance in an inner chamber of the inner barrel. The mixed substance in the inner barrel is then delivered by the syringe with subsequent needle retraction.

20 Claims, 23 Drawing Sheets

Related U.S. Application Data

(60) Provisional application No. 61/831,017, filed on Jun. 4, 2013.

(51) Int. Cl.
  *A61M 5/28* (2006.01)
  *A61M 5/32* (2006.01)

(52) U.S. Cl.
  CPC . *A61M 5/3234* (2013.01); *A61M 2005/31598* (2013.01); *A61M 2005/3231* (2013.01); *A61M 2005/3236* (2013.01)

(56) References Cited

U.S. PATENT DOCUMENTS

| | | | |
|---|---|---|---|
| 3,662,753 A | | 5/1972 | Tassell |
| 3,739,947 A | | 6/1973 | Baumann et al. |
| 3,749,084 A | * | 7/1973 | Cucchiara ......... A61B 5/02755 600/575 |
| 3,872,864 A | * | 3/1975 | Allen, Jr. ......... A61M 5/31596 604/89 |
| 4,188,949 A | | 2/1980 | Antoshkiw |
| 4,411,163 A | | 10/1983 | White |
| 4,643,723 A | | 2/1987 | Smit |
| 4,655,747 A | * | 4/1987 | Allen, Jr. .............. A61M 5/284 604/191 |
| 4,820,275 A | | 4/1989 | Haber et al. |
| 4,834,714 A | | 5/1989 | Lascar et al. |
| 5,078,691 A | | 1/1992 | Hamacher |
| 5,211,285 A | | 5/1993 | Haber et al. |
| 5,300,030 A | | 4/1994 | Crossman et al. |
| 5,312,336 A | * | 5/1994 | Haber ................. A61M 5/2448 604/191 |
| 5,395,326 A | | 3/1995 | Haber et al. |
| 5,496,284 A | | 3/1996 | Waldenburg |
| 5,593,391 A | | 1/1997 | Stanners |
| 5,643,206 A | | 7/1997 | Fischer |
| 5,807,323 A | | 9/1998 | Kriesel et al. |
| 5,851,197 A | | 12/1998 | Marano et al. |
| 5,885,256 A | | 3/1999 | Chern et al. |
| 6,027,482 A | | 2/2000 | Imbert |
| 6,132,400 A | | 10/2000 | Waldenburg |
| 6,248,095 B1 | | 6/2001 | Giambattista et al. |
| 6,387,078 B1 | | 5/2002 | Gilllespie, III |
| 6,491,667 B1 | | 12/2002 | Keane et al. |
| 6,793,646 B1 | | 9/2004 | Giambattista et al. |
| 7,112,188 B2 | | 9/2006 | Waldenburg |
| 7,169,132 B2 | | 1/2007 | Bendek et al. |
| 7,399,295 B2 | | 7/2008 | Waldenburg |
| 7,402,150 B2 | | 7/2008 | Matsumoto et al. |
| 7,935,087 B2 | | 5/2011 | Judd et al. |
| 8,021,333 B2 | | 9/2011 | Kaal et al. |
| 8,096,971 B2 | | 1/2012 | Bassarab et al. |
| 8,945,048 B2 | | 2/2015 | Thorley et al. |
| 9,539,393 B2 | | 1/2017 | Johannesson et al. |
| 2002/0035348 A1 | | 3/2002 | Hjertman |
| 2002/0183690 A1 | | 12/2002 | Arnisolle |
| 2004/0097874 A1 | | 5/2004 | Griffiths et al. |
| 2004/0236273 A1 | | 11/2004 | Tanaka et al. |
| 2005/0154357 A1 | | 7/2005 | Pinel |
| 2005/0277886 A1 | | 12/2005 | Hommann et al. |
| 2006/0111666 A1 | | 5/2006 | Homann et al. |
| 2007/0270710 A1 | | 11/2007 | Frass et al. |
| 2009/0234298 A1 | * | 9/2009 | Habeshaw ......... A61M 5/2033 604/195 |
| 2010/0047914 A1 | | 2/2010 | Peyman et al. |
| 2010/0094214 A1 | | 4/2010 | Abry et al. |
| 2010/0106138 A1 | | 4/2010 | Chavarria |
| 2010/0249753 A1 | | 9/2010 | Gaisser et al. |
| 2010/0298811 A1 | | 11/2010 | Connair |
| 2012/0053516 A1 | | 3/2012 | Cronenberg et al. |
| 2013/0060231 A1 | | 3/2013 | Adlon et al. |
| 2013/0060232 A1 | | 3/2013 | Adlon et al. |
| 2014/0358091 A1 | | 12/2014 | Johannesson et al. |

FOREIGN PATENT DOCUMENTS

| | | |
|---|---|---|
| JP | 2-302265 A | 12/1990 |
| TW | 201125609 A | 8/2011 |
| WO | WO 2000/062839 A2 | 10/2000 |
| WO | WO 2002/072171 A2 | 9/2002 |
| WO | WO 2005/013830 A1 | 2/2005 |
| WO | WO 2005/072801 A1 | 8/2005 |
| WO | WO 2006/058435 A2 | 6/2006 |
| WO | WO 2006/108243 A2 | 10/2006 |
| WO | WO 2006/119570 A1 | 11/2006 |
| WO | WO 2008/087071 A1 | 7/2008 |
| WO | WO 2009/003234 A1 | 1/2009 |
| WO | WO 2010/135732 A1 | 11/2010 |
| WO | WO 2011/060541 A1 | 5/2011 |
| WO | WO 2011/075760 A1 | 6/2011 |
| WO | 2014197602 A1 | 12/2014 |

OTHER PUBLICATIONS

U.S. Appl. No. 14/296,194, filed Jun. 4, 2014.
European Patent Office, International Search Report in International Patent Application No. PCT/US2014/040917, dated Oct. 17, 2014 (6 pages).
European Patent Office, Written Opinion of the International Searching Authority in International Patent Application No. PCT/US2014/040917, dated Oct. 17, 2014 (8 pages).

\* cited by examiner

ACTUATION MECHANISMS FOR DUAL CHAMBER MIXING SYRINGES

CROSS-REFERENCE TO RELATED APPLICATIONS

This application is a continuation of U.S. patent application Ser. No. 14/296,194, filed Jun. 4, 2014, which claims priority to U.S. Provisional Patent Application No. 61/831,017, filed on Jun. 4, 2013, which is included by reference herein in its entirety for all purposes.

FIELD

THIS INVENTION relates to mixing devices for syringes. More particularly, this invention relates to an actuation mechanism for a dual chamber mixing syringe which enables storage, mixing, and injection of one or more pharmaceutical substances.

BACKGROUND

It is known to provide syringes that comprise a mixing device for mixing deliverable substances prior to injection. This allows, for example, a diluent to be added to a dehydrated, lyophilized, desiccated or powdered active substance immediately prior to injection, which is particularly useful for substances that are subject to degradation or loss of activity when stored in a hydrated form.

The majority of mixing devices for syringes utilize sequential chambers, wherein the syringe has one barrel having a first proximal chamber and a second distal chamber separated by, for example, a membrane or elastomeric seal. A number of such sequential-chamber mixing syringes utilize a bypass protrusion at a section of the barrel to enable fluid in the proximal chamber to bypass the dividing membrane and mix with the fluid or powder in the distal chamber.

However, some mixing syringes utilize concentric barrel configurations. The concentric barrel mixing syringes to date, however, require complex assemblies, multiple operation steps by the user, or other particular nuances that make them difficult to manufacture, assemble, or operate. For examples, some existing concentric barrel mixing syringes require concentric inner and outer barrels that are selectively rotatable with respect to each other, and require one or more sealing rings which contain a passage means therein. The barrels must be rotated to align a hole in the inner barrel with the passage means in a sealing ring. The passage means in the sealing ring includes a radially extending opening through the sealing ring and a groove extending longitudinally of the sealing ring from the radially extending opening. This arrangement being such that the groove connects the outer barrel with the radially extending opening and the radially extending opening selectively connects the groove with the hole in the inner barrel. This enables flow of fluid from the outer barrel into to the inner barrel to thereby mix the fluid with a substance in the inner barrel. Such configurations require complex components and cumbersome requirements for the user to operate the device.

Other concentric barrel designs utilize outer and inner telescopic tubular elements seated inside a barrel and coaxial with the longitudinal axis. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon. Accordingly, such mixing syringe configurations require three tubular elements, with the outer and inner concentric chambers residing inside a third barrel.

There are numerous complexities associated with the use of concentric barrels for mixing syringe configurations. In addition to those described above, mixing syringes utilizing concentric barrels must also address factors such as maintenance of container sterility, interaction of components for sealing, venting requirements, and distribution of internal forces, among others. Some dual chambered syringes have concentric inner and outer barrels that form an annular space to hold a fluid and utilize one or more apertures between the inner and outer barrels to enable flow of a liquid from the annular space into the inner barrel and thereby mix the liquid with a substance in the inner barrel. The liquid is forced from the annular into the inner barrel by depression of a plunger slidably movable in the annular space. First and second sealing bands are slidably received about the inner barrel in the annular space and are mutually spaced therealong. The position of the sealing bands can dictate how sterility of the fluid path is maintained, how internal forces are distributed, and how venting occurs. For example, both of the sealing bands may be initially positioned above the aperture to form a sealed annular volume for the first liquid component. Because of this arrangement, the aperture also must act as a vent to enable any air in the annular space distal to the second sealing band, which space must be sterilized, to be expelled via the aperture upon depression of the plunger. This venting requirement may cause difficulties and require additional equipment and processing steps, such as requiring filling the inner chamber under vacuum to remove all air from the inner chamber and the distal portion of the outer barrel below the second reconstitution seal.

Generally, prior art mixing devices comprising concentric barrels are complicated in structure and often require rotation of the barrels to align one or more apertures that enable a flow of a liquid substance from one chamber into another. Further to this, various sterility, sealing and venting arrangements have been used which have serious limitations in terms of ease of manufacture and operation of the mixing device.

SUMMARY

It is therefore an object of the invention to provide an automatic mixing device and/or a syringe comprising the automatic mixing device that alleviates one or more of the problems associated with prior art mixing devices and/or syringes, such as those referred to above.

An aspect of the invention provides an actuating device removably mountable to a mixing device for a syringe, said mixing device comprising one or more seals, the actuating device comprising a housing releasably connectable to the mixing device, a rotatable trigger member, a biasing member, a delivery plunger and a mixing plunger releasably engaged with the trigger member in an initially locked state and engageable with at least one of the one or a plurality seals of the mixing device, wherein said rotatable trigger member is operable to initiate said biasing member to facilitate depression of said mixing plunger when engaged with said at least one of the one or more seals.

Another aspect of the invention provides an automatic mixing device comprising an actuating device removably mountable to the mixing device for a syringe, said mixing device comprising one or more seals, the actuating device comprising a housing releasably connectable to the mixing device, a rotatable trigger member, a biasing member, a delivery plunger and a mixing plunger releasably engaged with the trigger member in an initially locked state and engageable with at least one of the one or plurality of seals of the mixing device, wherein said rotatable trigger member is operable to initiate said biasing member to facilitate depression of said mixing plunger when engaged with said at least one seal.

Yet another aspect of the invention provides an automatic mixing syringe comprising a mixing device and an actuating device removably mounted thereto and a needle assembly, said mixing device comprising one or more seals, the actuating device comprising a housing releasably connectable to the mixing device, a rotatable trigger member, a biasing member, a delivery plunger and a mixing plunger releasably engaged with the trigger member in an initially locked state and engageable with at least one of the one or plurality of seals of the mixing device, wherein said rotatable trigger member is operable to initiate said biasing member to facilitate depression of said mixing plunger when engaged with said at least one seal.

Suitably, the actuating device is mountable or mounted to the mixing device in an initially locked state. Suitably, the trigger member is rotatable clockwise and/or anticlockwise to initiate said biasing member to facilitate depression of said mixing plunger when engaged with said at least one seal.

In an embodiment, the mixing plunger comprises one or more prongs initially engaged with the trigger member in the initial locked state. Preferably, this engagement is through engageable interaction between the prongs or portions thereof and one or more trigger engagement members. The trigger engagement members may be slots, ledges, recesses, detents or the like. Suitably, the biasing member is initially retained in an energized state between the trigger member and the mixing plunger. In at least one embodiment, the biasing member is initially retained within an interior chamber of the trigger member and bearing upon a sleeve plateau of the mixing plunger. Upon rotation of the trigger member, the mixing plunger is disengaged from the trigger member and caused to translate axially by expansion of the biasing member from its energized state. Axial translation of the mixing plunger in the distal direction causes the axial translation of said at least one seal of the mixing device. Preferably said at least seal is a proximal seal. In a preferred form, upon rotation of the trigger member, the one or more prongs of the mixing plunger are respectively disengaged from corresponding, respective trigger member slots, whereby the mixing plunger is caused to translate axially by expansion of the biasing member from its energized state. Preferably, the mixing plunger comprises one or more sleeve members. Axial translation of the mixing plunger in the distal direction causes the sleeve members to bear upon and axially translate said at least one seal of the mixing device, as described above The housing may comprise an interior locking surface that in the initially locked state prevents or impedes axial travel of the delivery plunger. The interior locking surface may comprise one or more abutments, projections, vanes, tabs or the like that can initially engage the delivery plunger to prevent or impede axial travel of the delivery plunger and subsequently slidably engage respective channels in the delivery plunger to permit axial travel of the plunger. In an embodiment, the delivery plunger is coupled to the trigger member so that rotation of the trigger member when activating the actuation device co-ordinately rotates the plunger member. Suitably, this rotation moves the plunger into a position or orientation whereby the interior locking surface of the housing is in slidable engagement with the plunger channels, thereby permitting axial travel of the delivery plunger.

In one embodiment, further rotation of the trigger member can be prevented or impeded subsequent to rotation to activate mixing. In one particular embodiment, the trigger comprises one or more trigger lock members that can engage one or more respective, complementary housing lock members. Suitably, rotation of the trigger member when activating the actuation device rotates the trigger lock into engagement with the housing lock members to thereby prevent or impede further rotation of the trigger member.

In one embodiment, rotation of the mixing plunger relative to the housing may be at least partly impeded or prevented. Suitably, this may be achieved by way of the mixing plunger and the housing comprising interacting members such as one or a plurality of ridges, ribs, channels, grooves or the like.

In at least one embodiment, the mixing device and/or the automatic mixing syringe comprises a sealing membrane that maintains the sterility of the mixing device prior to operation, wherein said membrane is removable by or during the operation of the actuating device, mixing device and/or the automatic mixing syringe. Preferably, the sealing membrane is removable. The sealing membrane may be manually removed such as through a pull-tab motion by the user. In another embodiment, the sealing membrane may be removed by indirect action by the user, such as by user activation of the actuating device. In one such embodiment, user activation of the actuating device causes a component of the actuating device, such as the sleeve members, to axially translate and at least partially remove or puncture the membrane from the mixing device. Additionally or alternatively, a component of the actuating device, such as a distal tip of the delivery plunger, may be used to pierce the membrane. Such a configuration permits the sterility of the mixing device to be maintained prior to operation of the actuating device or use of the automatic mixing syringe. In a preferred form, the sealing membrane is discoidal and puncturable by the delivery plunger. Notably, the delivery plunger is a component of the actuating device. Such a configuration permits the sterility of the mixing device to be maintained prior to operation of the actuating device, mixing device or use of the automatic mixing syringe.

In a particular embodiment, the mixing device further comprises an outer barrel and an inner barrel in a substantially coaxial relationship. Preferably, the outer barrel and the inner barrel are concentric. Suitably, the inner barrel and the outer barrel are non-rotatable with respect to each other. Suitably, the actuating device is removably mountable or mounted to the outer barrel. In one particular embodiment, the outer barrel comprises a barrel extension to which the actuating device is removably mountable or mounted. Removable mounting may be by way of a snap fit or interference fit, a screw thread or a bayonet coupling, although without limitation thereto. The barrel extension may be mounted to the outer barrel, or integrally formed with the outer barrel. The barrel extension may, optionally, include finger flanges or grips, or may alternatively have optional finger flanges or grips connected thereto.

In an embodiment, the inner barrel comprises an inner chamber. In an embodiment, an outer chamber is located in an annular space between the inner barrel and the outer barrel. According to this embodiment, the one or more seals of the mixing device are axially moveable within the outer chamber. Suitably, said mixing device is capable of comprising a plurality of mixing substances. Suitably, at least a first mixing substance is locatable in the outer chamber and at least a second mixing substance is locatable in an inner chamber in said inner barrel. In an embodiment, the inner barrel comprises one or more fluid paths through which the first mixing substance can enter the inner chamber in the inner barrel to thereby form a mixture with the second mixing substance.

The one or more fluid paths may comprise one or more apertures, holes, bores, ports, pass-throughs or conduits. These may be of any suitable shape, configuration, arrangement and/or number. Preferably, the fluid path comprises a plurality of apertures. The apertures may be radial bores (i.e., normal to the axis of the barrel), angular bores (i.e., at an angle to axis of the barrel), helical (e.g., an angular and radial path as it traverses the thickness of the barrel wall), or any number of other configurations. The number and placement of the apertures, in locational spacing and arrangement, may also be adjusted for the desired mixing characteristics. As such, these parameters of the apertures may be configured to promote the desired mixing, dilution, and other fluid flow characteristics of the mixing syringe. Suitably, the mixing device may comprise one or more components described in International Publication WO2013/020170, which is incorporated by reference in its entirety for all purposes.

The first and second mixing substances may comprise one or more fluids or one or more solids. The first mixing substance locatable in the outer chamber may be a fluid. The fluid may be a pharmaceutically active fluid or a pharmaceutically inactive fluid, such as a diluent. The second mixing substance locatable in the inner chamber may be a pharmaceutically active solid or a pharmaceutically active or inactive fluid. In one embodiment, the inner chamber contains a pharmaceutically active solid and the outer chamber contains a pharmaceutically inactive diluent, such as water, whereby entry of the diluent through the one or more apertures from outer chamber into the inner chamber facilitates mixing with the pharmaceutically active solid. The interaction between the diluent and the pharmaceutically active solid enables reconstitution of the pharmaceutically active solid for subsequent delivery to a patient. In another embodiment, the inner chamber contains a pharmaceutically active solid and the outer chamber contains a pharmaceutically active fluid, whereby entry of the fluid through the one or more apertures from the outer chamber into the inner chamber facilitates mixing with the pharmaceutically active solid in the inner chamber. The interaction between the pharmaceutically active fluid and the pharmaceutically active solid enables reconstitution of the pharmaceutically active solid for subsequent delivery to a patient. In yet another embodiment, the inner chamber contains a first pharmaceutically active fluid and the outer chamber contains a second pharmaceutically active fluid, whereby entry of the first pharmaceutically active fluid through the one or more from the outer chamber into the inner chamber facilitates mixing with the second pharmaceutically active fluid in the inner chamber. While the operation of the actuating device, mixing device, and the automatic mixing syringe are described with reference to a fluid moving from an outer chamber to an inner chamber, such description is meant only as an exemplary fluid transfer between the outer and inner chambers and the opposite is also possible. Accordingly, the present invention also provides for devices and syringes which facilitate the transfer of fluids from the inner chamber to the outer chamber. Additionally, the fluid transfer between inner and outer chambers can be configured to occur once or repeated, due to the "closed system" configuration possible by the embodiments of the present invention. In another of these configurations, the interaction between the first pharmaceutically active fluid and the second pharmaceutically active fluid enables mixing of the pharmaceutically active fluids for subsequent delivery to a patient. Similarly a liquid diluent and a liquid pharmaceutically active fluid may be stored and mixed to dilute the pharmaceutically active fluid for subsequent delivery to a patient. Accordingly, the mixing device may facilitate the storage of multiple component pharmaceutical substances in the outer and inner chambers, thereby maintaining the stability and efficacy of the pharmaceutical substances during transport and over prolonged periods of storage.

In a further embodiment, the mixing device comprises one or more vents in fluid communication with said outer chamber. Preferably, the one or more vents are operable to facilitate exit of air from the outer chamber to atmosphere when the mixing plunger and distal seal are slidably moved in the outer chamber. The one or more vents may be integrally formed in said outer barrel or may be a vent cap mounted or affixed to said inner and/or outer barrel. In either embodiment, conduits, holes, porous membranes, collapsible components and the like may be utilized. For example, in at least one embodiment the vent cap is a plastic vent cap comprising one or more vent conduits, which plastic vent cap closes the outer chamber at the distal end of the outer barrel while permitting air to pass through the one or more vent conduits to atmosphere upon depression of the mixing plunger.

Suitably, the mixing device comprises said at least one seal located in said outer chamber which is capable of axial movement from a first position in sealing engagement with said one or more fluid paths in the inner barrel to a second position at least partly between said one or more fluid paths and said one or more vents. In a preferred form, the mixing device comprises a plurality of seals. In one particular form, the plurality of seals comprises a proximal seal and a distal seal. Suitably, said at least one seal is the distal seal. In a preferred embodiment, the plurality of seals comprises: a proximal seal engageably or connectably coupled to, connectable or affixed to, or otherwise adjacent to the one or more sleeves of the mixing plunger and slidably moveable in the outer chamber; and said distal seal initially in a first position in sealing engagement with said one or more fluid paths in the inner barrel and slidably moveable in the outer chamber from sealing engagement with the one or more fluid paths to a second position intermediate or at least partly between said one or more fluid paths and said vent. The movement of the one or more sleeve members of the mixing plunger causes movement of the proximal seal to which the sleeve members are engaged or adjacent to. This movement is relayed to the first mixing substance in the outer chamber and, similarly, to the distal seal. In at least one embodiment, the movement of the one or more sleeve members, the proximal seal and, accordingly, the first mixing substance in the outer chamber is relayed to the distal seal by pneumatic pressure or force created in the first mixing substance by the motion of the mixing plunger seal. Accordingly, axial movement of the one or more sleeve members indirectly (i.e., without needing direct contact) facilitates axial movement of the distal seal to said second position.

In one or more embodiments of the present invention include a vent cap which may optionally have internal vent cap features which facilitate the desired positioning of the distal seal during operation of the mixing device. The internal vent cap features may be, for example, posts, prongs, flex arms, or the like which are configured to correctly position the distal seal upon translation within the outer chamber, with reference to the one or more apertures, to enable substantially all of the first substance within the outer chamber to be passed-through to the inner chamber. The apertures between the outer and inner chambers are desired to remain open to allow movement of the first substance until substantially all of the first substance is pushed out of the outer chamber by the mixing plunger seal. This may be achieved by the compressibility of the seals themselves. Additionally or alternatively, the dimensions and the flexing capabilities of the internal vent cap features may be configured to align the distal seal with the apertures to ensure that substantially all of the first substance within the outer chamber to be passed-through to the inner chamber.

Suitably, the one or more sleeve members of the actuating device are axially moveable within the outer chamber between the outer barrel and the inner barrel. The one or more sleeve members of the mixing plunger may facilitate entry of the at least first mixing substance into the inner chamber in the inner barrel and to facilitate axial movement of the distal seal from a first position in sealing engagement with said one or more fluid paths in the inner barrel to said second position intermediate or at least partly between said one or more fluid paths and said vent, as described above.

In one embodiment, the automatic mixing syringe further comprises one or more removable safety caps. Preferably, the removable safety caps prevent undesired operation of the mixing device. In at least one embodiment, the removable safety cap prevents, specifically, undesirable movement of the distal seal prior to use (e.g., during transportation). Removable of the safety cap may permit further function of the mixing device, after mixing, by function of the mixing device and the movement of the distal seal, has been completed. The removable safety cap may comprise a plurality of protrusions which are insertable through respective vent conduits so as to be adjacent to, or in contact with, the distal seal.

In at least one embodiment, the mixing syringe further comprises one or more covers. For example, the mixing syringe may include a proximal cover and a distal cover. In at least one embodiment, a distal cover may, optionally, connect with the removable safety cap to facilitate removal of the safety cap. The proximal cover may be a separate disposable component which may be removed to expose the trigger member and plunger for operation, or may be a component that is integrated into the trigger member and/or plunger. For example, in at least one embodiment, the proximal cover may be rotatable itself to rotate the trigger member and activate the actuating device, as described above.

The syringe may be utilized for storing, transporting, mixing, and injecting one or more mixing substances to treat a patient. As will be described further below, the syringe may further contain safety features which retract the needle after use, providing desirable needle-stick prevention, and prevent re-use of the syringe. Suitably, the plunger of the actuating device is slidably moveable within the inner barrel of the mixing device to thereby facilitate delivery of the mixed substances or mixture to a user, patient or other recipient.

In an embodiment, the automatic mixing syringe may comprise a retractable needle or needle assembly, referred to herein as a "retractable syringe". In a further embodiment, the delivery plunger may be utilized to activate a retraction mechanism of the automatic mixing syringe.

It will be appreciated that the retractable syringe may comprise any needle retraction mechanism that is operable with the invention disclosed herein. By way of example, the needle retraction mechanism may be as described in International Publication WO2006/119570, International Publication WO2006/108243, International Publication WO2009/003234 and International Publication WO2011/075760, and/or U.S. Pat. No. 8,702,653 and International Application PCT/US2014/024781, although without limitation thereto.

In one broad form, the automatic mixing syringe is a retractable syringe that comprises a needle assembly mounted thereto, such as at a distal end of an inner chamber of the mixing device or syringe, wherein the needle assembly comprises an energized biasing member (such as a compressed spring), release of said biasing member facilitates retraction of the retractable needle. In a particular embodiment, the retractable needle is a component of a needle retraction mechanism that includes a needle subassembly including a cannula and a needle-over-mold through which the cannula extends. The needle retraction mechanism may be at least partly housed within a barrel adapter mounted to a barrel tip. Suitably, the retractable needle is adapted to move from an injection position in which the needle extends from a distal end of the barrel or barrel tip to a retracted position in which the needle is disposed at least partly within the barrel or barrel tip. An actuator subassembly includes a needle seal, a push bar and at least one actuating surface, the push bar being disposed at least partially proximal to the needle seal. The actuator subassembly further comprises at least one biasing member (e.g., a compressed spring) and an actuable locking arrangement disposed to maintain the biasing member in an energized position when the locking arrangement is locked. Suitably, actuation of release of the locking arrangement releases the biasing member, the biasing member being disposed to move the needle from the injection position to the retracted position when the biasing member is released from the energized position. Suitably, the locking arrangement is actuable by depression of the plunger and contact of the plunger seal with the push bar. A non-limiting example of this embodiment is described in International Application PCT/US2014/024781.

In an alternative embodiment of this broad form, the needle assembly may be similar to that disclosed in U.S. Pat. No. 8,702,653 which does not require a needle body and which activates retraction of the cannula through contact between the delivery plunger seal and a needle seal.

In another broad form, the automatic mixing syringe is a retractable syringe wherein the delivery plunger, or a delivery plunger seal, can engage the retractable needle, whereby release of the at least partially energized biasing member of the actuation device (i.e., after activation of mixing) facilitates retraction of the retractable needle when engaged by the delivery plunger. Suitably, the delivery plunger is engaged or engageable with a delivery plunger seal. Preferably, the delivery plunger seal is mountable or mounted to the plunger of the actuating device after the trigger member has been utilized, the distal seal has been axially translated, and the mixing of fluids has occurred, after which the delivery plunger is utilized to deliver the mixed fluid through the needle and then utilized to activate or facilitate retraction of the needle. Preferably, the delivery plunger seal is capable of engaging the retractable needle to retract the needle. In one embodiment, the delivery plunger may cause flexible housing prongs to detach from an initially locked engagement with the trigger member. Upon such disengagement, the biasing member may be permitted to expand from its energized or partially (or reduced) energized state in the proximal direction, causing the trigger member to axially translate proximally.

Preferably, the needle assembly may further comprise a needle seal that retains the retractable needle, wherein the cannula of the retractable needle passes through the needle seal to permit delivery of the mixed substances or mixture to a user, patient, or other recipient. Suitably, the retractable syringe comprises one or more delivery plunger locking systems to prevent axial translation of the needle in the distal direction after retraction of the delivery plunger seal and the needle engaged therewith.

As described herein, the one or more prongs of the mixing plunger co-operate with the trigger member to maintain the biasing member in an initially energized state. Disengagement of the one or plurality of prongs from the trigger member facilitates release of stored energy from the biasing member. In an embodiment, the mixing plunger further comprises arms that comprise projections that slidably engage grooves in an inner wall of the housing, such as during axial movement of the mixing plunger relative to the housing. In an embodiment, a body portion of the mixing plunger comprises one or more guides that slidably engage grooves in an inner wall of the housing, such as during axial movement of the mixing plunger relative to the housing. The projections or guides, and their slidable engagement with the inner wall of the housing, may be utilized to prevent axial rotation of the mixing plunger with reference to the housing.

Non-limiting examples of needle retraction mechanisms according to this broad form are described in International Publication WO2006/119570, International Publication WO2006/108243, International Publication WO2009/003234 and International Publication WO2011/075760. According to one embodiment, the retractable syringe comprises: a needle assembly comprising the retractable needle, wherein the retractable needle comprises a cannula and a needle seal engageable by the plunger seal mounted to the plunger inner. Preferably, the needle assembly is configured such that the needle seal retains the retractable needle and the cannula of the retractable needle passes through the needle seal to permit delivery of the mixed substances or mixture to a user, patient, or other recipient. In one embodiment, the needle assembly is similar to that disclosed in International Publication WO2011/075760 which includes a needle body that is capable of being captured or engaged by the delivery plunger seal, such as within a recess within the delivery plunger seal, for retraction into the barrel or inner chamber of the syringe.

In yet another aspect, the invention provides a method of assembling a syringe comprising an automatic mixing device including the step of removably mounting an actuating device to a mixing device of the syringe so that a sleeve of the actuating device is operable to depress a mixing plunger seal of the mixing device. In one embodiment, the method includes the step of releasably connecting or coupling a housing of the actuating device to an outer barrel of the mixing device. In one embodiment, the method includes the step of releasably connecting or coupling a housing of the actuating device to an outer barrel of the mixing device. In one embodiment, the method further includes, prior to step (i), affixing a vent cap comprising the one or more vents to a portion of the inner barrel that is located distally of the one or more apertures. Preferably, the distal end of the outer barrel is connected to the vent cap. In a further embodiment, the method further includes the step of attaching a removable or pierceable membrane to the proximal end of the inner barrel of the mixing device prior to attachment of the actuating device to the mixing device. In a preferred embodiment, the removable or pierceable membrane is attached in a manner such that it is removed automatically by operation of the sleeve of the actuating device, i.e., axial translation of the sleeve in the distal direction. Preferably, the method further includes the step of inserting a needle assembly into the inner chamber located distally of the one or more apertures.

In a further aspect, the invention provides a method of manufacturing a syringe including the step of removably mounting an actuating device to a mixing device mounted to a syringe.

In a still further aspect, the invention provides a method of operating a syringe comprising an automatic mixing device, said method including the steps of:
(i) operating an actuating device of the automatic mixing device to facilitate mixing a plurality of substances;
(ii) connecting a plunger of the actuating device to a delivery plunger seal of the mixing device;
(iii) operating the plunger to deliver the substances mixed at step (i) to a recipient.

Preferably, operation of the actuating device removes or pierces a membrane from attachment to the mixing device. In one embodiment, the method includes the step of unlocking the plunger prior to step (iii). Unlocking the plunger may occur between steps (i) and (ii) in at least one embodiment or between steps (ii) and (iii) in other embodiments of the invention.

In another embodiment, the method of operating a syringe comprising an automatic mixing device further includes: (iv) activating a needle retraction mechanism to retract the needle into the syringe. Preferably, the activation of the needle retraction mechanism occurs after substantially all of the substances are delivered to the recipient.

According to various aspects and embodiments described herein, reference is made to a "biasing member", such as in the context of an actuating device biasing member and a delivery plunger biasing member. It will be appreciated that the biasing member may be any member which is capable of storing and releasing energy. Non-limiting examples include a spring inclusive of a coiled spring and a leaf spring, a resiliently compressible or elastic band or other member. Preferably, the biasing member is a spring such as a compressible spring.

In embodiments relating to the actuating device and automatic mixing device, the spring is maintained in an initially compressed state. According to this embodiment, decompression of the spring forces the sleeve to move axially relative to the housing and bear against the mixing plunger, thereby causing depression of the mixing plunger. In at least one embodiment, the spring is also utilized to axially translate the plunger after it has activated a retraction mechanism to retract the needle assembly into the barrel of the mixing device. According to this embodiment, decompression of the spring forces retraction of the delivery plunger seal and retractable needle coupled thereto.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

The present invention provides an actuating device with an integrated plunger which may be mounted or otherwise connected to a dual chamber mixing device for storing, transporting, mixing, and injecting a mixed drug substance to a patient. The actuating device may be incorporated as part of an automatic mixing device and/or syringe, or removably attached to a mixing device to produce an automatic mixing syringe. In one or more of these embodiments, the actuating device and/or plunger thereof may be utilized to facilitate moving, piercing, or removal of a membrane at the proximal end of the mixing device. The membrane, as is described further herein, may be a sterile barrier utilized to maintain container integrity of the mixing device prior to operation of the device. Accordingly, the novel actuating devices of the present invention aid in maintenance of the sterility of the mixing device, and at least partial moving, piercing, or removal of the membrane prior to operation of the device and/or syringe for drug injection.

While the embodiments described herein may describe certain components of the automatic mixing syringe, actuating device and mixing device as separate components, these may readily be manufactured as integrally formed or unitary components. Similarly, while the embodiments described herein may describe certain components of the automatic mixing syringe, actuating device and mixing device as integrally formed or unitary components, these may readily be manufactured as separate components that are subsequently assembled before use.

Figure 1:
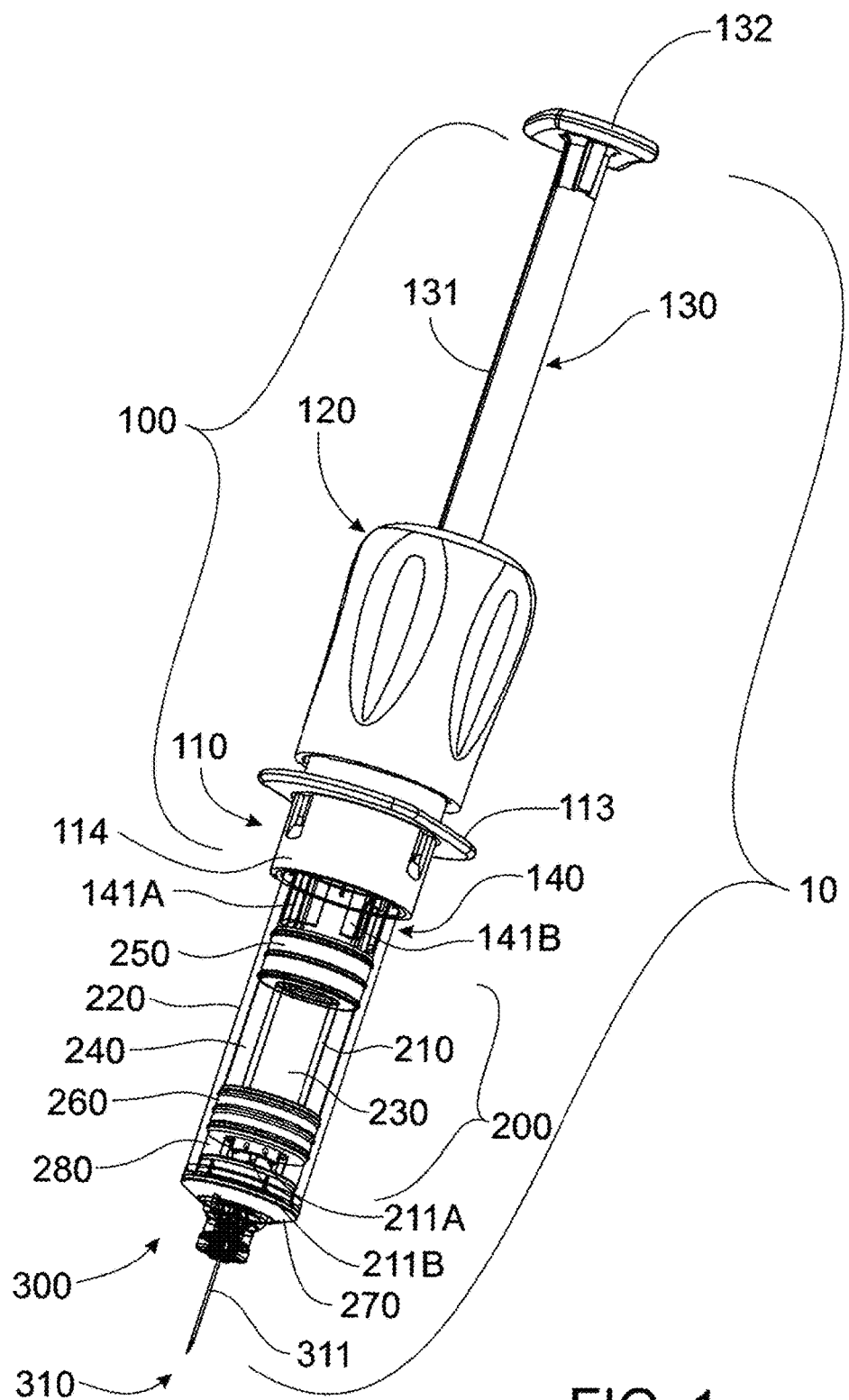
FIG. 1 shows an isometric view of an embodiment of an automatic mixing syringe comprising an actuating device coupled to a mixing device, according to one embodiment of the present invention.
Figure 2:
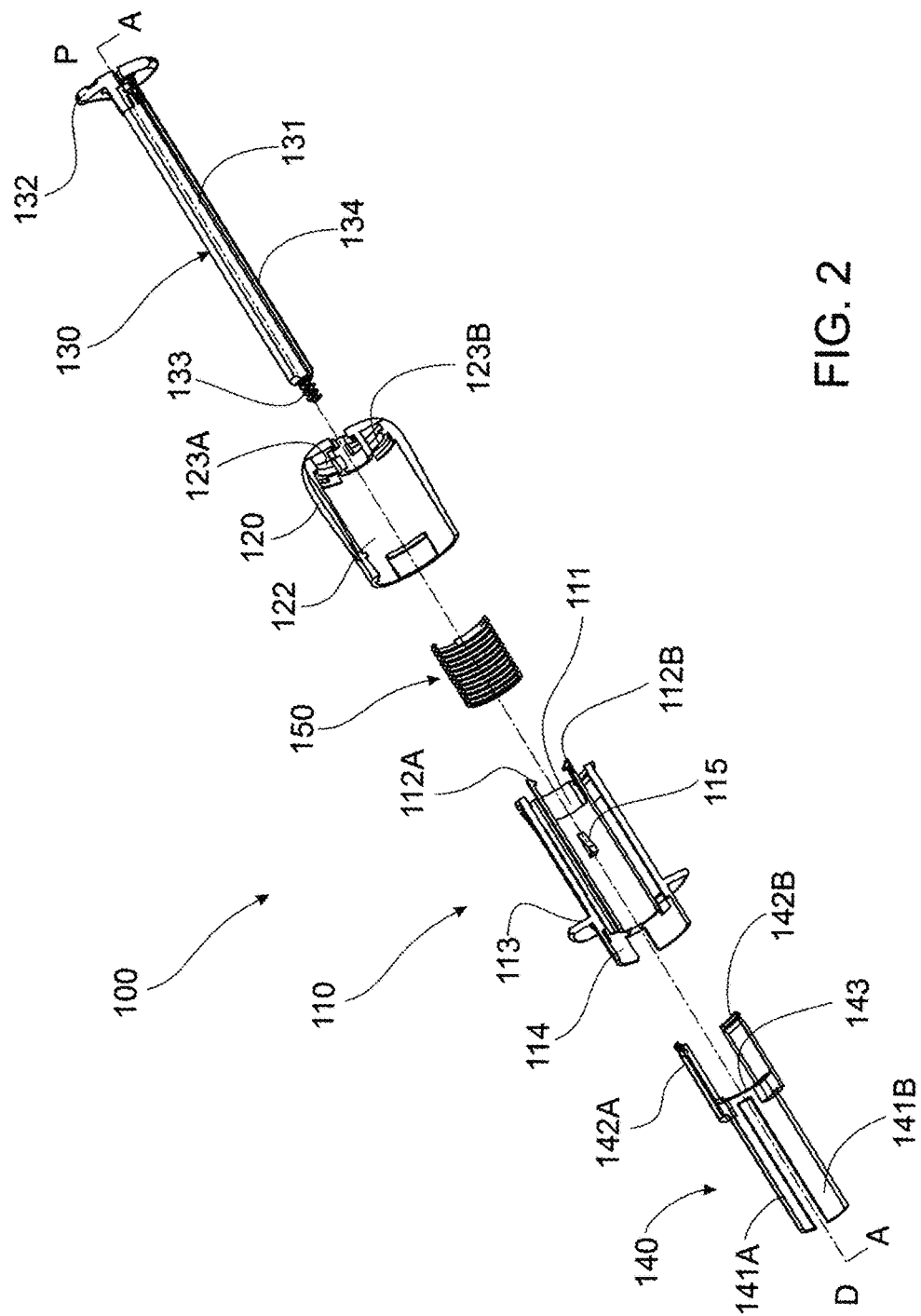
FIG. 2 shows an exploded view of the actuating device shown in FIG. 1.
Figure 3A:
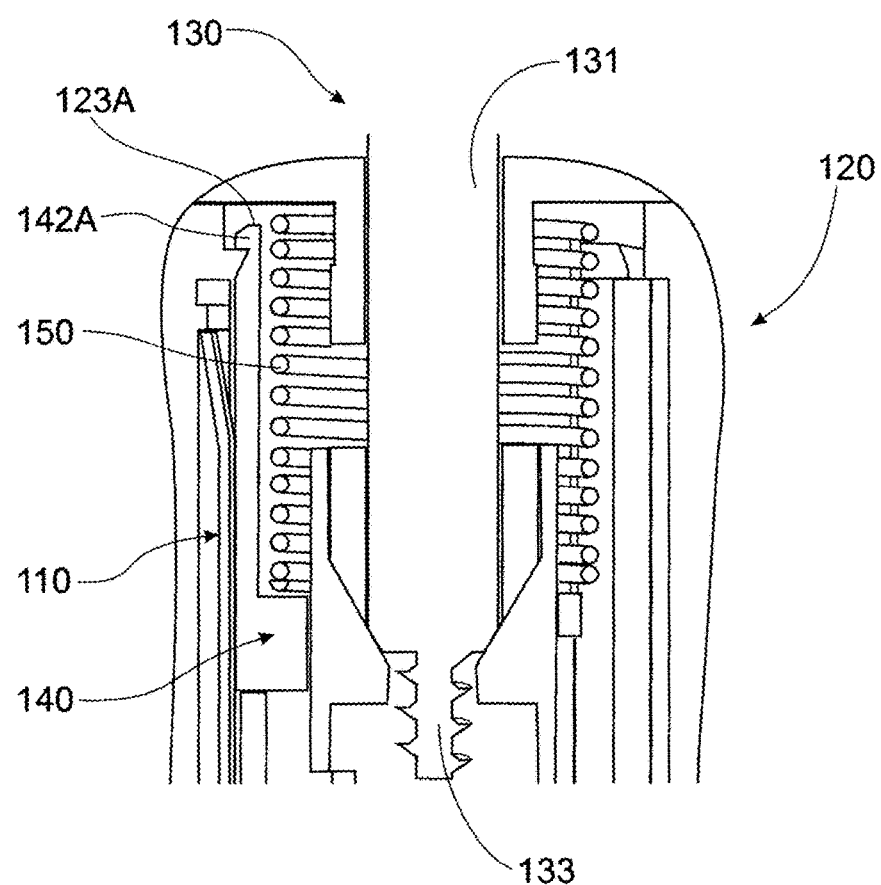
FIG. 3A shows a cross-sectional view of the embodiment shown in FIG. 2 with the actuating device having a locked trigger member.
Figure 3B:
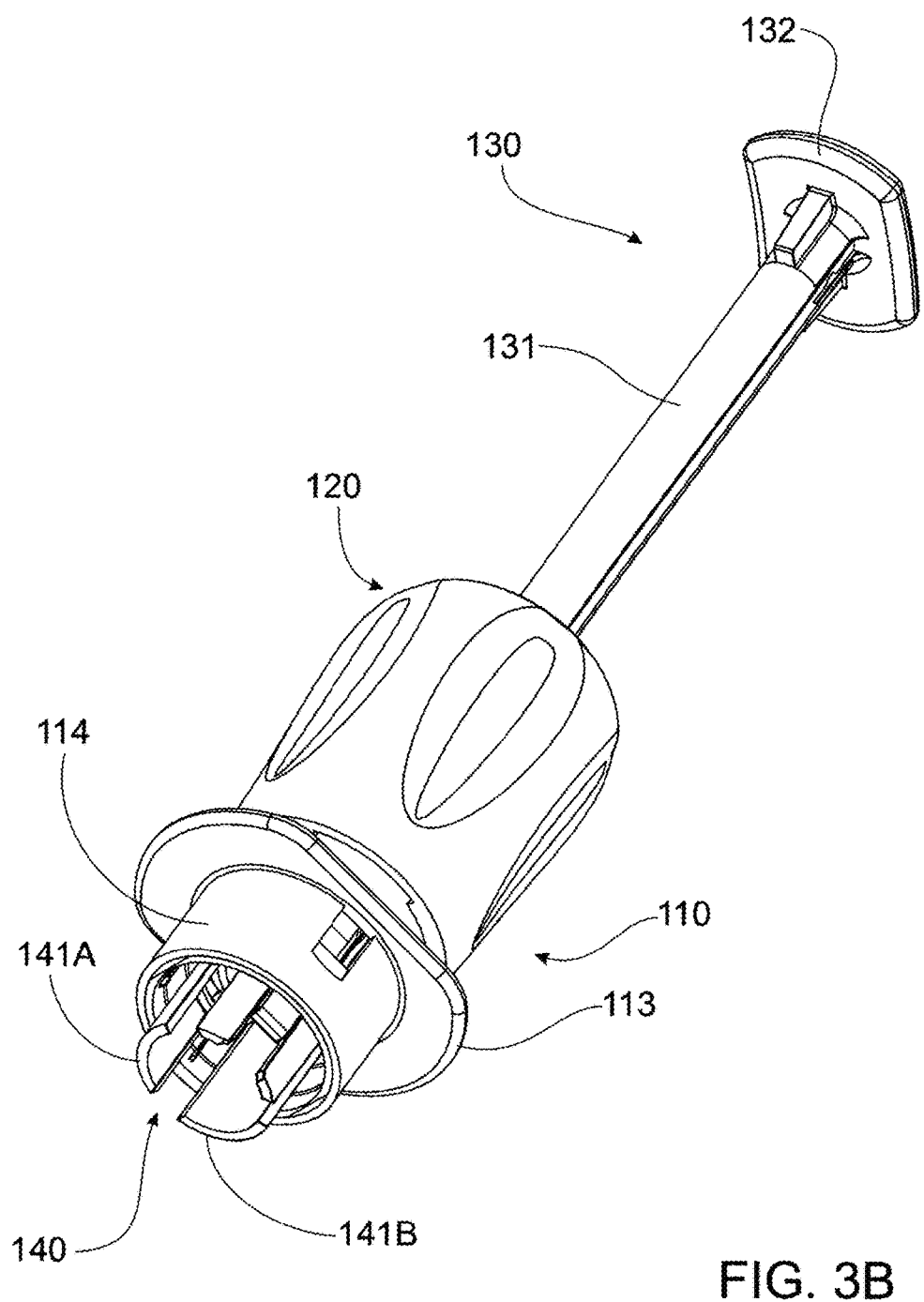
FIG. 3B shows an isometric view of the embodiment shown in FIG. 3A.
Figure 3C:
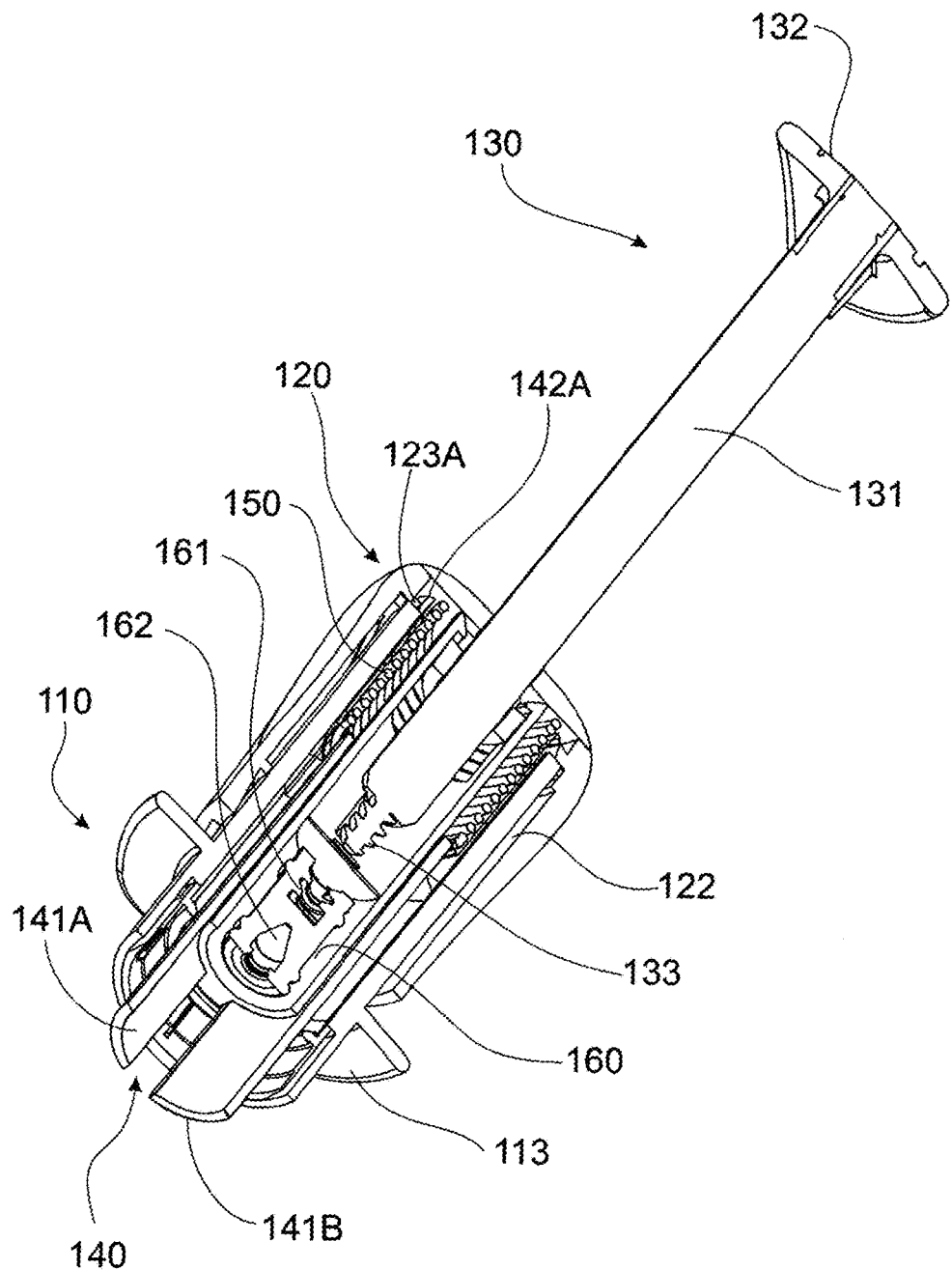
FIG. 3C shows a cross-sectional view of the embodiment shown in FIG. 3B.

Referring to FIG. 1, automatic mixing syringe 10 comprises actuating device 100, mixing device 200 and needle assembly 300. Mixing device 200 has dual concentric inner and outer barrels 210, 220. Inner chamber 230 is located within inner barrel 210 and outer chamber 240 is located between outer barrel 220 inner barrel 210. Reference is also made to FIG. 2 which shows an exploded view of an embodiment of actuating device 100 comprising housing 110 and trigger member 120 which is mountable to housing 110 and FIGS. 3A-C which show the assembled actuating device 100. Housing 110 further comprises opening 111, housing prongs 112A,B, flange 113 and housing mount 114. A delivery plunger 130 comprising shaft 131 comprising button 132 and seal-engaging member 133 is configured to pass through an opening, such as an axial opening 121 of the trigger member 120 and an axial opening 111 of the housing 110 such that it may axially translate, as will be described in more detail hereinafter. Trigger member 120 further comprises interior chamber 122 lock and trigger slots 123A, B. Mixing plunger sleeve 140 comprises sleeve members 141A, B, prongs 142A, B and sleeve plateau 143. Biasing member 150 in this embodiment is a spring which is initially compressed (i.e., energized) prior to activation of the actuating device 100. Referring again to FIG. 1, it will be appreciated that while plunger 130 is capable of axial translation within inner chamber 230 of the mixing device 200 and mixing plunger 140 is capable of axial travel within outer chamber 240 of mixing device 200, this is initially prevented or impeded until rotation of the trigger member 120, which will be described hereinafter. As shown in FIGS. 3A-3C, in at least one embodiment of the present invention the trigger member 120 is mounted at least partially upon and substantially concentric with the housing 110 of the actuating device 100, such that the trigger member 120 may be axially rotated and/or translated thereupon. FIGS. 3A and 3C show a releasable locking arrangement between the mixing plunger 140 and trigger member 120. The mixing plunger 140 is initially engaged with the trigger member 120 through releasably engageable interaction between prongs 142A, B and corresponding trigger member slots 123A, B. The biasing member 150 is initially retained in an energized state between the trigger member 120 and the mixing plunger sleeve 140. In at least one embodiment, the biasing member 150 is initially retained within an interior chamber 122 of the trigger member 120 and bearing upon a sleeve plateau 143 of the mixing plunger 140.

Figure 3D:
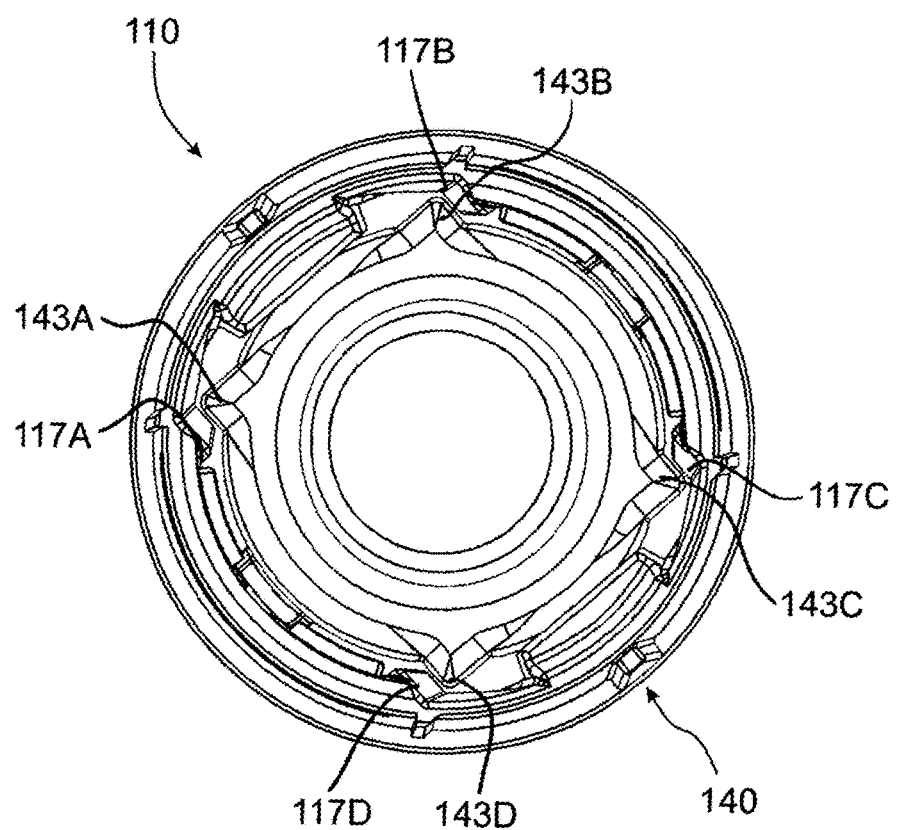
FIG. 3D shows an end view of coupling between a trigger member and mixing plunger of an embodiment of an actuating device.

While trigger member 120 is rotatable (i.e., capable of clockwise or anticlockwise rotation) FIG. 3D shows that ribs 117A, B, C, D in housing 110 engage complementary ridges 143A, B, C, D in mixing plunger 140 to prevent rotation of mixing plunger 140, so that rotation of trigger member 120 is not accompanied by rotation of mixing plunger 140.

Referring also to FIG. 1, sleeve members 141A, B are configured to connect to, bear against or contact proximal seal 250 residing within outer chamber 240 between the outer barrel 220 and the inner barrel 210 of the mixing device 200. Distal seal 260 is also located in outer chamber 240 between the outer barrel 220 and the inner barrel 210 of the mixing device 200, the function of which will be described in more detail hereinafter. Mixing device 200 further comprises vent cap 270 mounted thereto. In this embodiment, distal seal 260 is located proximal to apertures 211A, B in inner barrel 210 which form respective fluid paths between the outer chamber 240 and the inner chamber 230. Vent chamber 280 is located distal to distal seal 260. As will be described in more detail hereinafter, manipulation and operation of the actuating device 100 facilitates the mixing of a first substance contained in the outer chamber 240 with a second substance contained in the inner chamber 230. The mixed substance may then be injected through the needle assembly 300 by axial translation of the delivery plunger 130, for drug delivery into a patient.

Figure 4A:
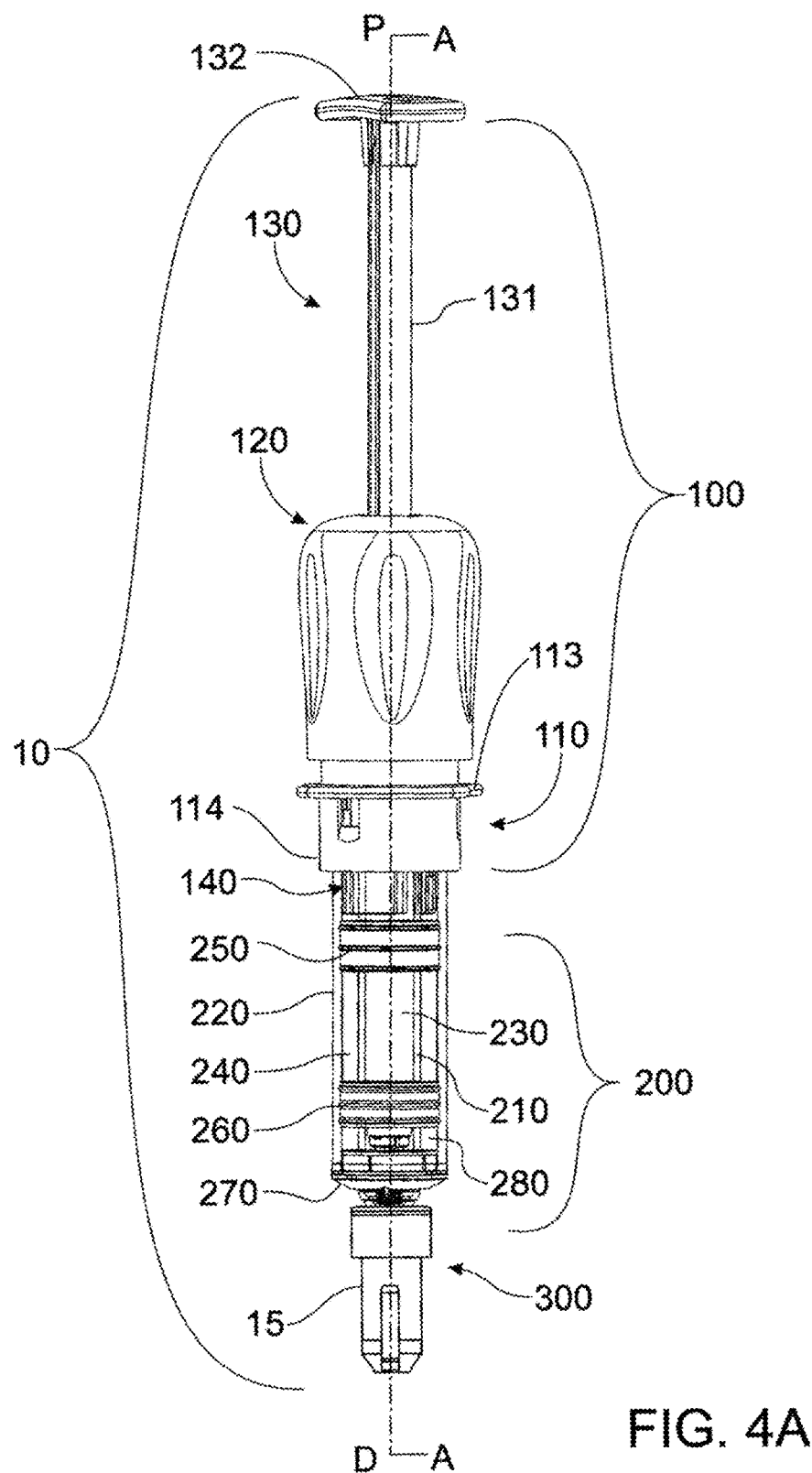
FIG. 4A shows a side view of the embodiment shown in FIG. 1 before the mixing plunger has been activated by the actuating device.
Figure 4B:
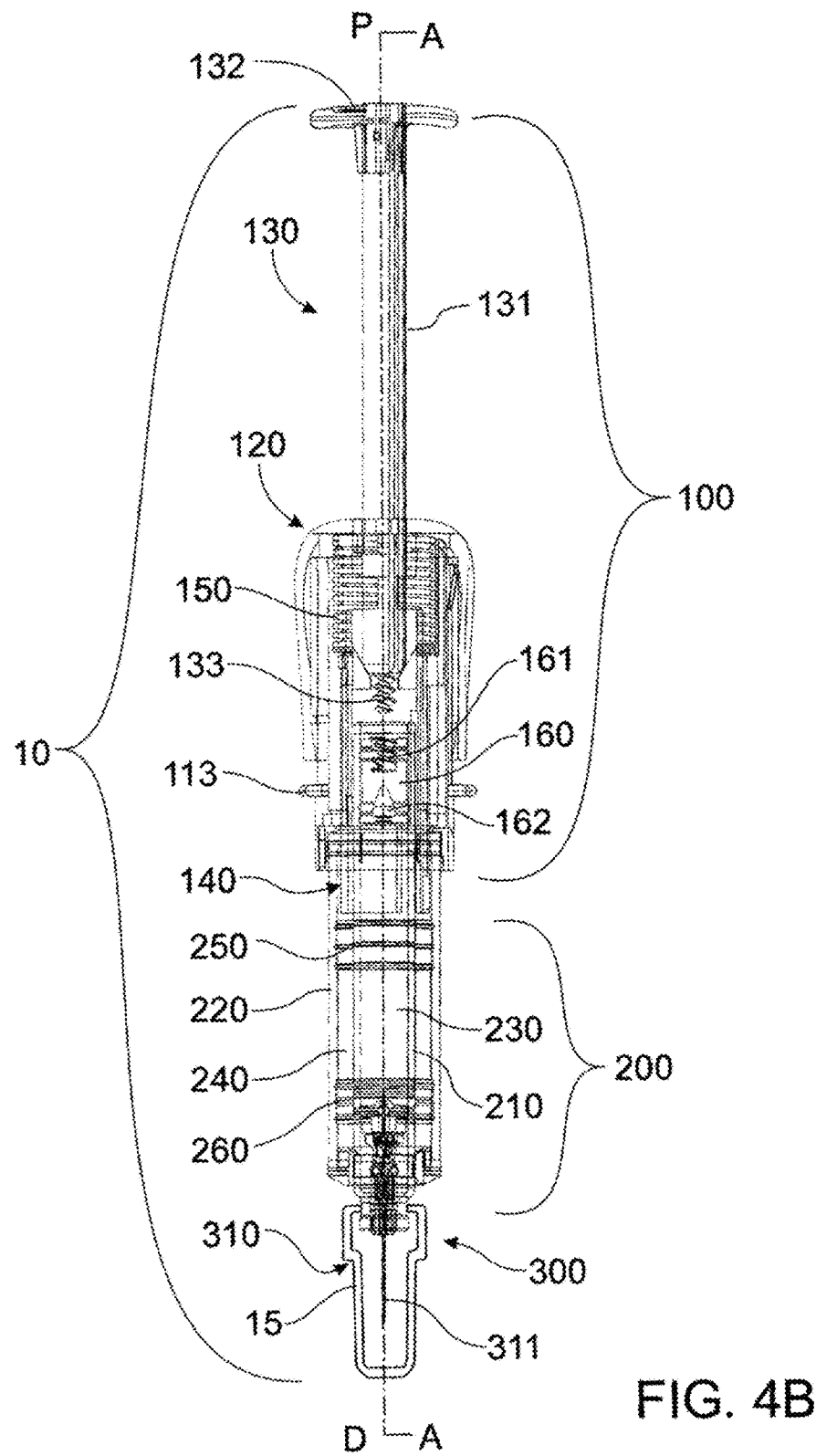
FIG. 4B shows a cross-sectional view of the embodiment shown in FIG. 4A.

FIGS. 4A and 4B show a side view and a cross-sectional side view of the embodiment shown in FIG. 1 and FIG. 2, in an initial locked configuration such as may be utilized for storage or transportation. Plunger 130 is incapable of axial translation within inner chamber 230 of the mixing device 200 and mixing plunger 140 is incapable of axial travel within outer chamber 240 of mixing device 200 until rotation of the trigger member 120, which will be described hereinafter. In this state, rigid needle shield 15 removably covers cannula 311. The actuating device 100 may be pre-formed with the mixing device 200 to produce an automatic mixing syringe 10, or the actuating device 100 and mixing device 200 may be separate structures that are connected or otherwise mounted together. In the latter embodiment, the mixing device 200 may comprise a mount upon which the housing 110 of the actuating device 100 may be connected. In at least one embodiment, the mount is located at the proximal end P of the outer barrel 220 of the mixing device 200. As described above, a mixing plunger 140 of the actuating device 100 is configured to at least partially reside and axially translate within outer chamber 240 of the mixing device 200. Axial translation of the mixing plunger sleeve 140 causes axial translation of the proximal seal 250 and thereby causes fluid transfer from the outer chamber 240 to the inner chamber 230 of the mixing device 200, as described further herein. The sleeve 140 is caused to axially translate by operation of a trigger member 120.

Figure 5A:
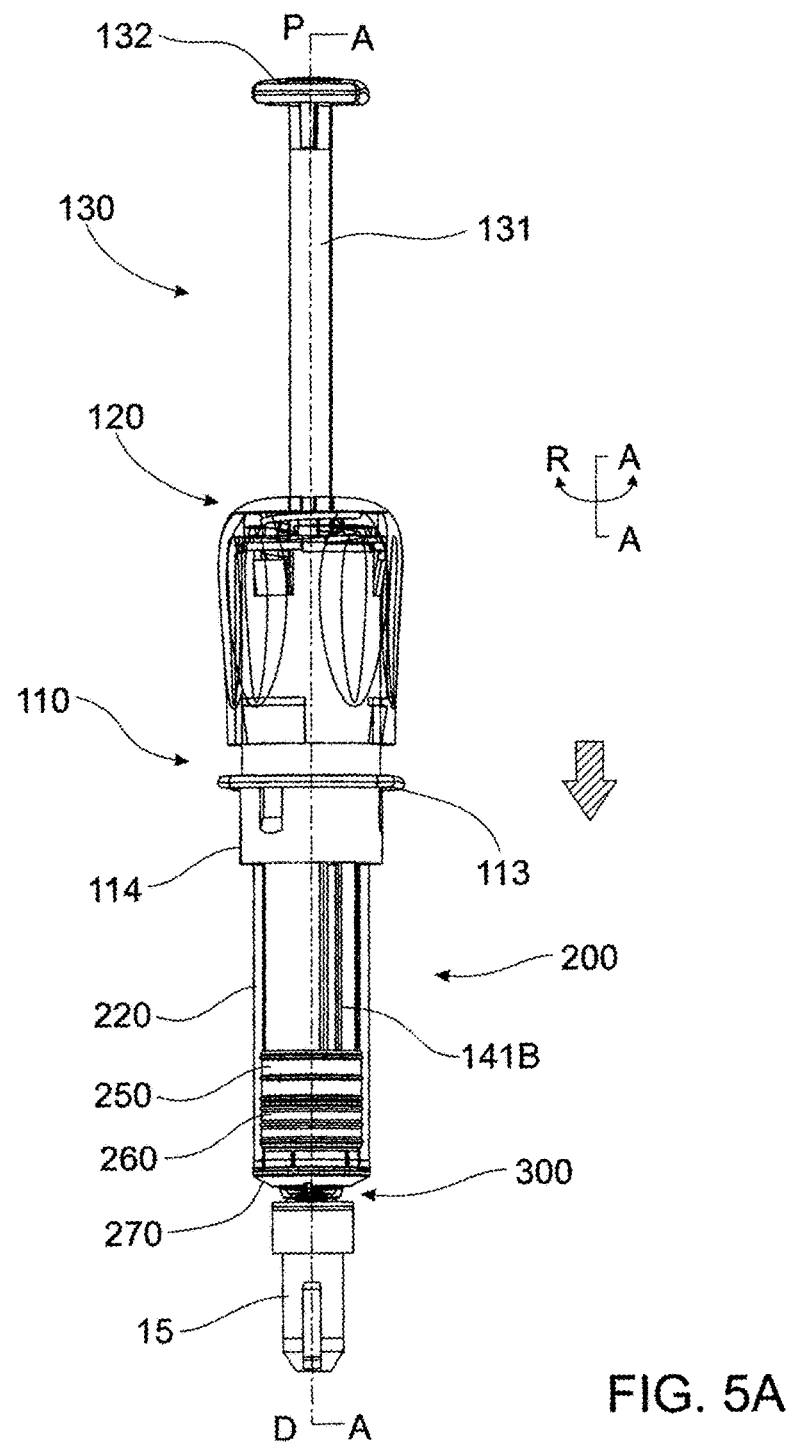
FIG. 5A shows a side view of the embodiment shown in FIG. 1 after the mixing plunger has been activated by the actuating device.
Figure 5B:
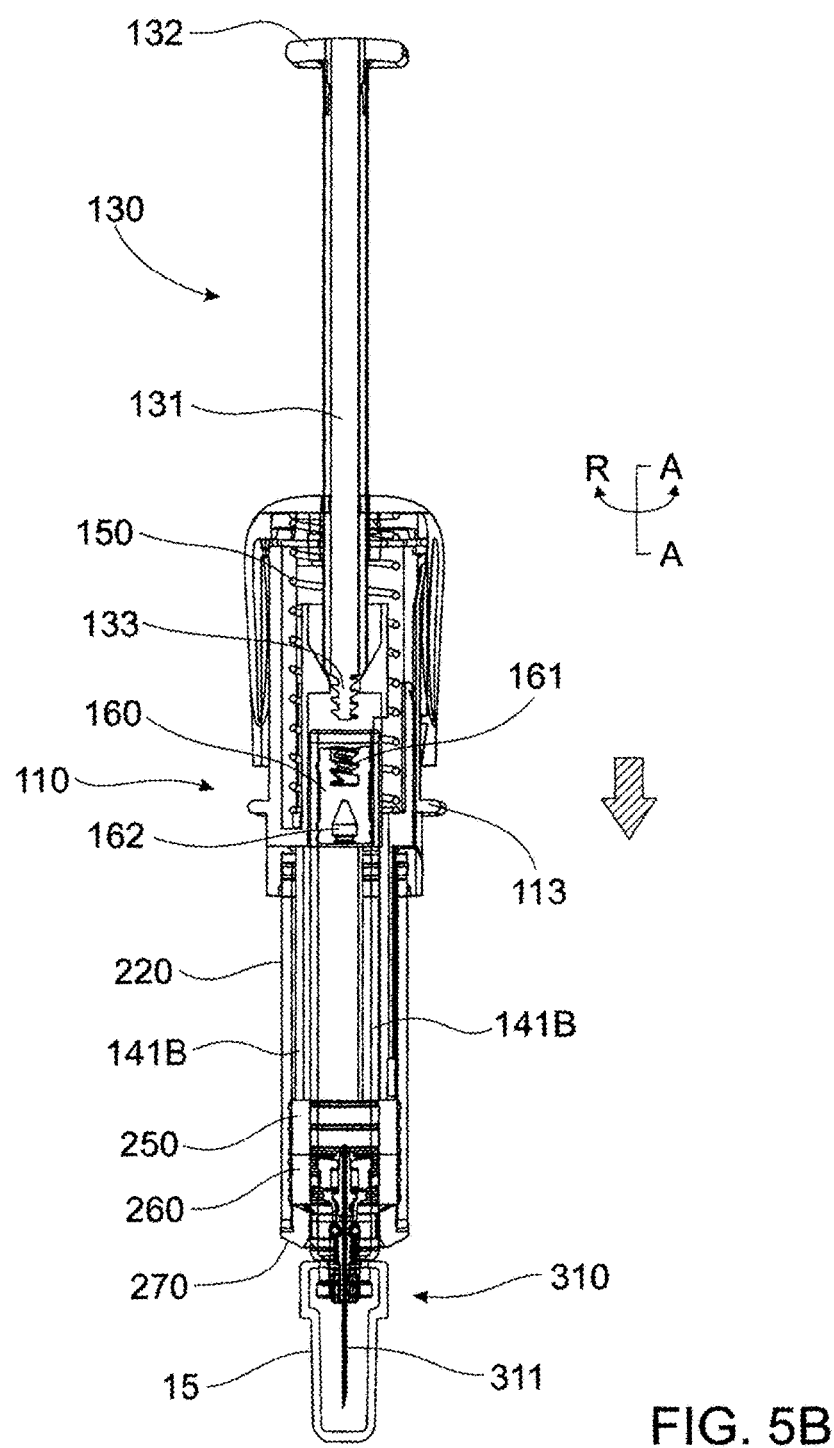
FIG. 5B shows a cross-sectional view of the embodiment shown in FIG. 5A.

FIGS. 5A and 5B show a side view and a cross-sectional side view of the embodiment shown in FIG. 1 following unlocking the trigger member 120 and activation of the actuating device 100. As shown, the trigger member 120 may be rotated clockwise or anticlockwise by a user to activate the actuating device 100. Upon activation, the mixing plunger 140 is detached from the trigger member 120, such as by disengagement between the prongs 142A, B and the trigger slots 123A, B, and caused to translate axially in the distal direction by expansion of the biasing member 150 from its initial energized state. Such axial translation of the mixing plunger 140 causes the sleeve members 141A, B to contact and axially translate the proximal seal 250 of the mixing device 100. Therefore, distal movement of the plunger member 140 of the actuating device 100 causes movement of the proximal seal 250 to which the sleeve members 141,B are engaged or bear against. A first mixing substance may be contained in outer chamber 240 between the outer barrel 220 and the inner barrel 210 and between the proximal seal 250 and the distal seal 260 in the outer chamber 240. The distal seal 260 may initially be in a first position at least partially above (i.e., proximal to) one or more apertures 211A, B that are in the inner barrel 210 between the outer chamber 230 and the inner chamber 240. Movement of the mixing plunger 140 and the proximal 250 seal is relayed to the first mixing substance in the outer chamber 240 and, similarly, to the distal seal 260. In at least one embodiment, the movement of the sleeve 140, the proximal seal 250 and, accordingly, the first mixing substance in the outer chamber 240 is relayed to the distal seal 260 by pneumatic pressure or force created in the first mixing substance by the motion of the proximal seal 250. Accordingly, axial movement of the mixing plunger 140 indirectly (i.e., without needing direct contact) facilitates axial movement of the distal seal 260 to a second position. Upon movement of the distal seal 260 to a second position (i.e., in the direction of the hatched arrow in FIG. 4A), the first mixing substance contained in the outer chamber 240 may pass-through the one or more apertures 211A, B and into the inner chamber 230 of the inner barrel 210.

Figure 6A:
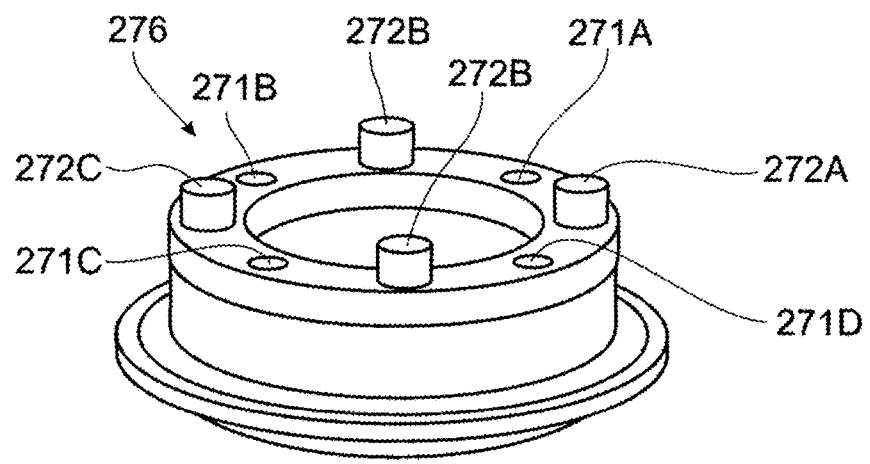
FIG. 6A shows an embodiment of a vent cap.
Figure 6B:
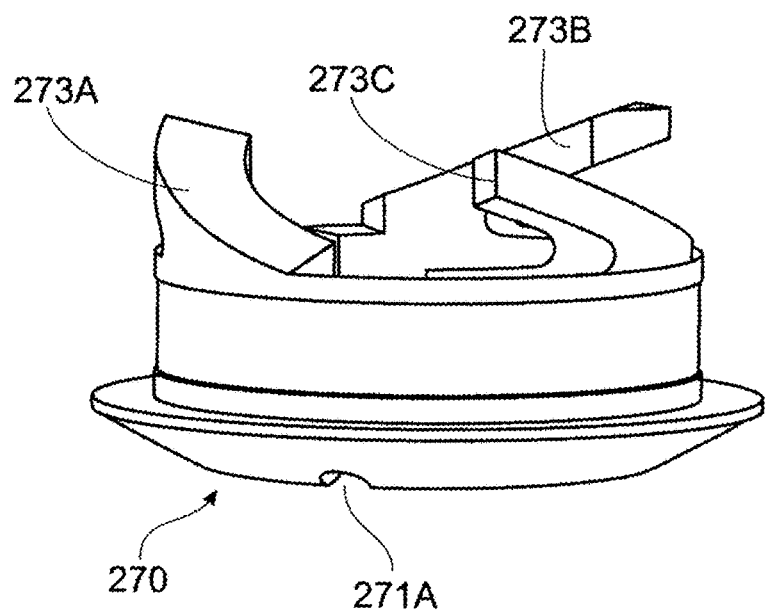
FIG. 6B shows another embodiment of a vent cap.

In some embodiments, vent cap 270 may be essentially as described in International Publication WO2013/020170 or International Publication WO2013/020170. Other embodiments of vent cap 270 are shown in FIGS. 15A and 15B, wherein the vent cap 270 may optionally have "internal" vent cap features locatable within outer chamber 240 which facilitate the desired positioning of the distal seal 260 during operation of the mixing device 100. The "internal" vent cap features may be, for example, projections such as posts, prongs, flex arms, or the like which are configured to correctly position the distal seal 260 upon axial translation within the outer chamber 240, with reference to the one or more apertures 211A, B, to enable substantially all of the first substance within the outer chamber 240 to be passed-through to the inner chamber. FIG. 6A shows an embodiment of the vent cap 270 having vents 271A, B, C, D and posts 272A, B, C, D, which would be internally located inside outer chamber 240. FIG. 6B shows an embodiment of the vent cap 270 having flex arms 273A, B, C which would be internally located inside outer chamber 240. The apertures 211A, B between the outer 240 and inner 230 chambers are desired to remain open to allow movement of the first substance until substantially all of the first substance is pushed out of the outer chamber 240 by the proximal mixing plunger seal 250. This may be achieved by the compressibility of the proximal seal 250 itself. Additionally or alternatively, the dimensions and the flexing capabilities of the internal vent cap features may be configured to align the distal seal 250 with the apertures 211A, B to ensure that substantially all of the first substance within the outer chamber 240 to be passed-through to the inner chamber 230. Accordingly, the distal seal 260 is permitted to float or self-adjust with reference to the apertures 211, B so that the apertures 211A. B remain open until the proximal mixing plunger seal 250 contacts the distal seal 260 and substantially all of the first substance is pushed out of the outer chamber 240 into the inner chamber 230 by the proximal mixing plunger seal 250.

It will be appreciated that the vent chamber 280 between the distal seal 260 and vent cap 270 is never in contact with any substance(s) in mixing device 200, hence there is no need to maintain sterility in vent chamber 280. Vent chamber 280 may fill with air, which is displaced out of the annular space between outer barrel 220 and inner barrel 210 and between the vents 271 of the vent cap 270 and the distal seal 260 upon depression of proximal seal 250 and axial movement of distal seal 260 Furthermore, because distal seal 260 initially covers apertures 211A, B in inner barrel 210, sterility of this fluid path between outer chamber 240 and inner chamber 230 is maintained during use of mixing device 200. Only distal seal 260 is potentially in contact with any non-sterile portion of outer barrel 220 and inner barrel 210, as fluid is caused to flow from outer chamber 230 into inner chamber 230 without ever contacting the non-sterile portion.

It will also be appreciated that automatic mixing syringe 10 is a "closed system," meaning there is no venting of the fluid path other than by needle injection. Accordingly, delivery plunger seal 160 may axially move in inner chamber 230 in the proximal direction in response to the distal movement of sleeve 140. This is because distal movement of the sleeve 140 against proximal seal 250 forces liquid from outer chamber 240 into the inner chamber 230 and increases the pressure and/or fluid volume within inner chamber 230. With rigid needle shield 15 still closed over the needle, there is no space for volume expansion other than to force delivery plunger seal 160 in the proximal direction within inner chamber 230. This is a desirable response as it provides visual and tactile indication to the user that the mixing has completed and that injection may be initiated.

Figure 7:
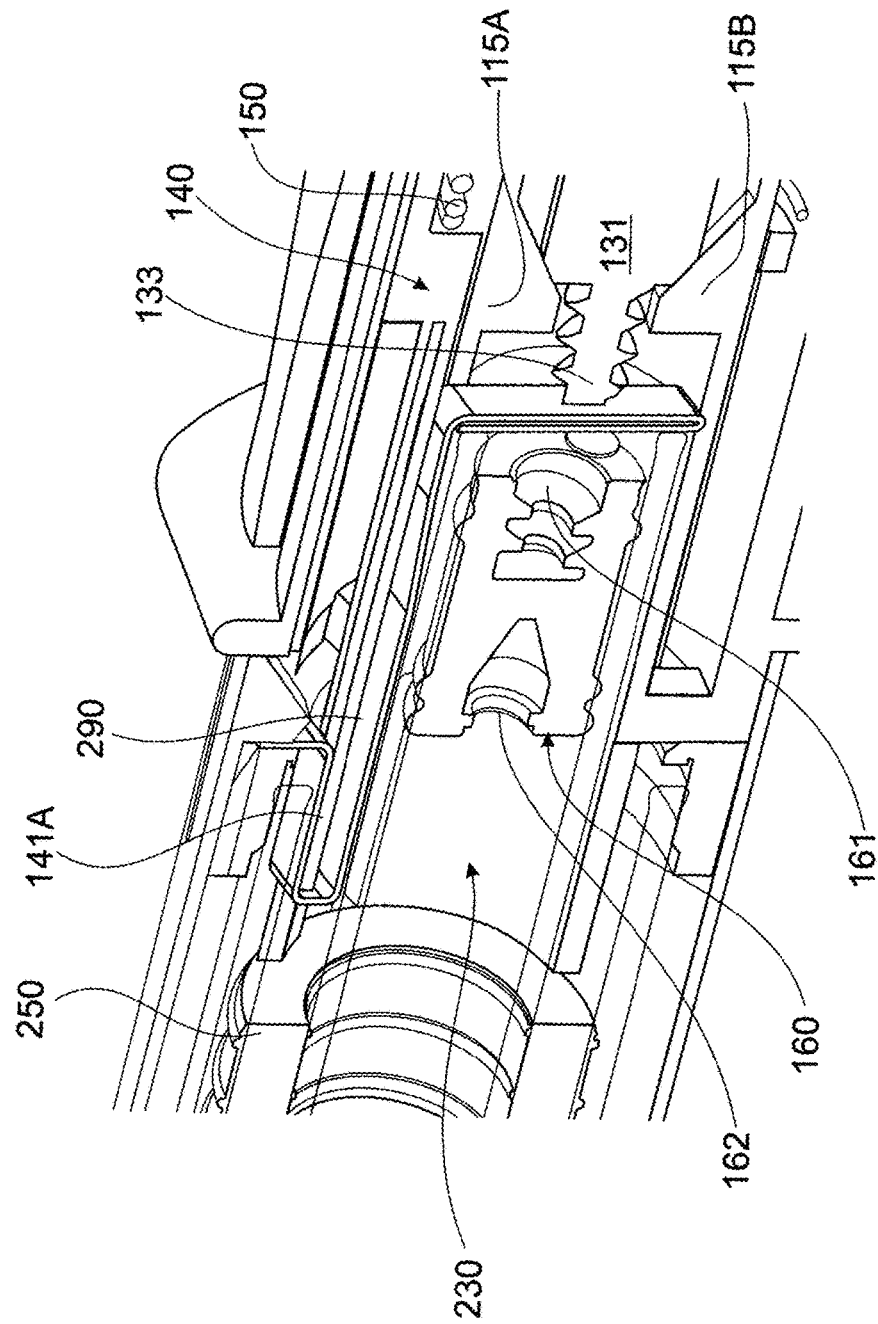
FIG. 7 shows an embodiment of a sealing membrane mounted to an automatic mixing device.

As described above, a sealing membrane 290 may initially reside at the proximal end of the mixing device 200, such as at the proximal end of the inner barrel 210, to cover the proximal end of the barrel(s) 210, 220 after assembly and filling with substance(s), but before connection to the actuating device 100. The sealing membrane 290 may be any of a variety of sterile fabrics and materials, such as TYVEK, used in the medical devices and pharmaceuticals industry. The sealing membrane 290 may be removed, pierced, or otherwise bypassed by operation of the actuating device 100 or automatically by the syringe user during operation. According to an embodiment shown in FIG. 7 as the sleeve 140 is axially translated in the outer chamber 240 to contact and displace the proximal seal 250. The sealing membrane 290 is configured to seal the proximal end of the inner barrel 210 and be removed by axial translation of the sleeve members 141A, B, as shown in FIG. 7. Concurrently with this action, as previously described proximal seal 250 is axially, slidably movable in outer chamber 240 of outer barrel 220 of mixing device 200 to thereby deliver the contents of the outer chamber 240 to the inner chamber 230 via one or more apertures 211A, B in the inner barrel 210. In an alternative embodiment, the sealing membrane 290 may be discoidal and located in the inner chamber 230 without extending or otherwise having a position located in the outer chamber 240 and contactable by mixing plunger 140. In this embodiment, the sealing membrane 290 is puncturable or pierceable by the delivery plunger 130 and is not contacted by the mixing plunger 140. A delivery plunger 130 configured for such a function is shown in FIG. 9E having, for example, a pointed distal tip to pierce the sealing membrane 290 and engage delivery plunger seal 160.

Figure 8A:
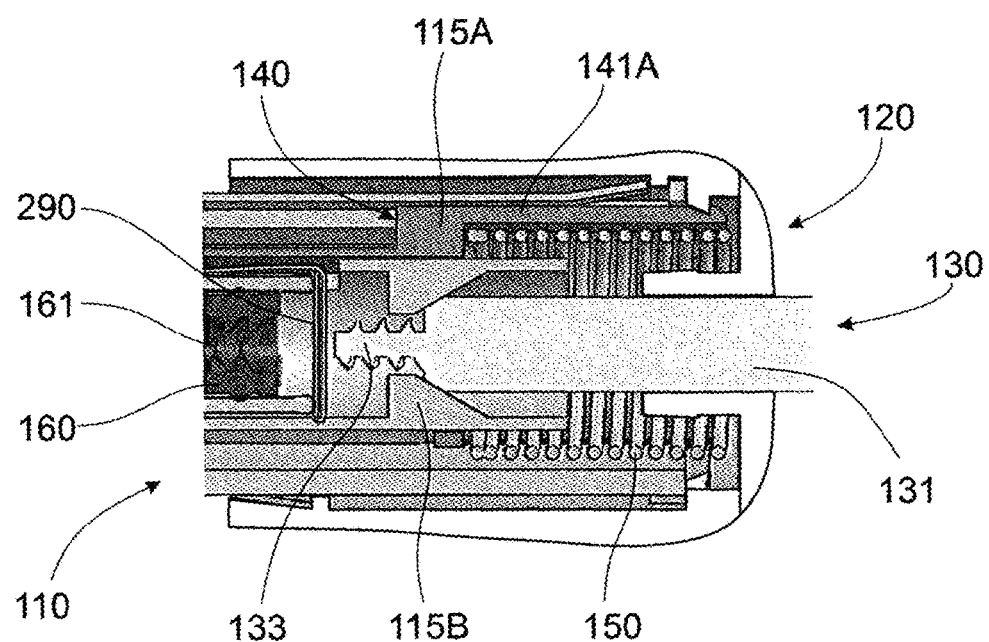
FIG. 8A shows a delivery plunger engaged by a housing to initially prevent axial travel of the delivery plunger.
Figure 8B:
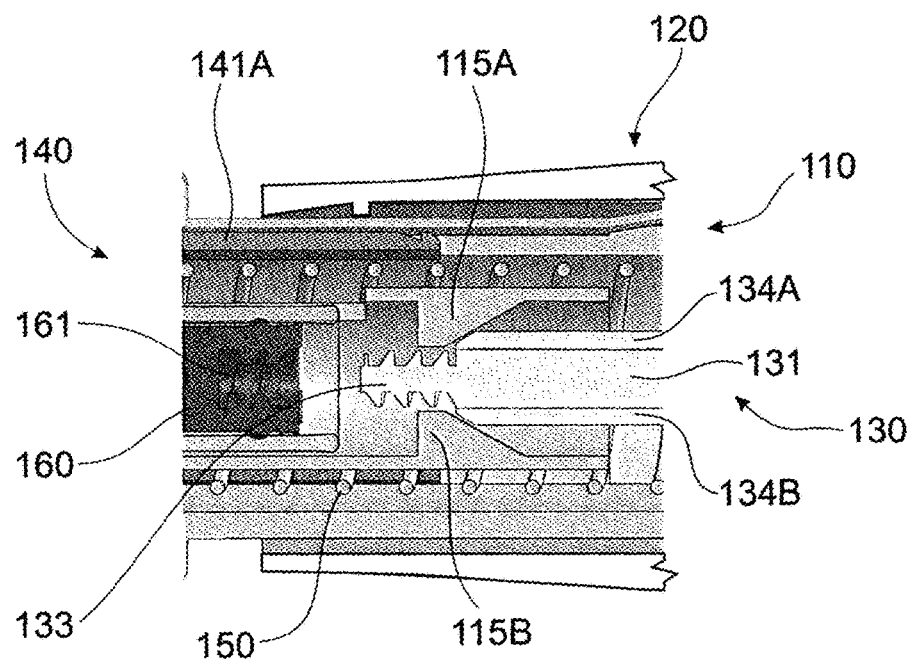
FIG. 8B shows a delivery plunger rotated into a position relative to the housing so as to be permitted to travel axially.

During rotation of trigger member 120 to disengage trigger member 120 and mixing plunger 140, delivery plunger 130 also rotates due to its connection with trigger member 120. This connection drives axial rotation of delivery plunger 130 when trigger member 120 is rotated and allows axial slidable travel of delivery plunger 130 within trigger member 120 once delivery plunger 130 is unlocked from housing 110. In the initial locked state of actuating device 100 shown in FIG. 8A abutments 115A, B of housing 110 bear against delivery plunger 130 to prevent axial travel of delivery plunger 130. Delivery plunger 130 is coupled to trigger member 120 so that rotation of trigger member 120 also rotates delivery plunger 130. This coupling may comprise any complementary mating portions that allow axial, slidable movement of the delivery plunger 130 within trigger member 120. FIG. 8B shows that when trigger member 120 is rotated (i.e., clockwise or anticlockwise) to activate mixing plunger 140, this rotation also aligns respective slots 134A, B in delivery plunger 130 with abutments 115A, 115B of housing 110 to thereby allow axial travel of delivery plunger 130 to deliver the mixed substances from inner chamber 230 to a recipient. It will be appreciated that abutments 115A, B have a longitudinal profile that allows the abutments 115A, B to fit in and slidably engage respective slots 134A, B in delivery plunger 130.

Figure 8C:
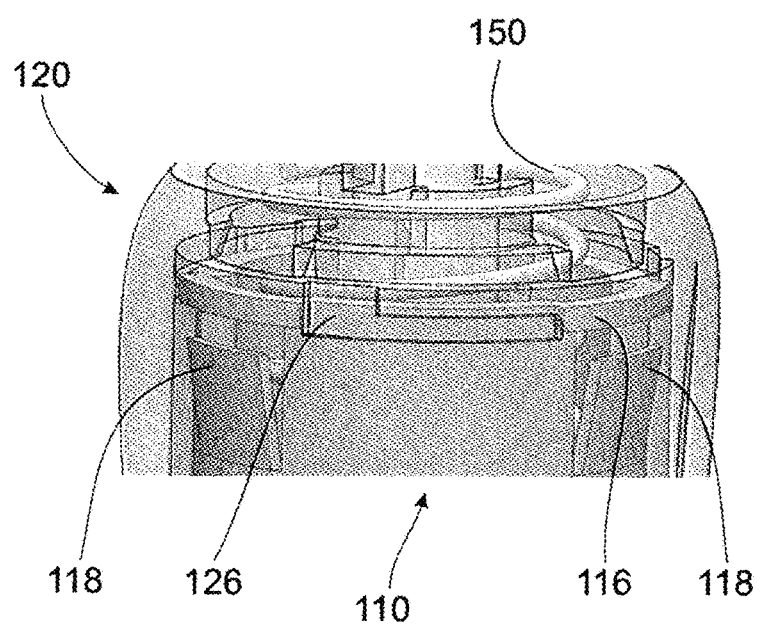
FIG. 8C shows an embodiment of a rotation lock formed between a trigger member and housing after rotation of the trigger member to activate mixing.

In one embodiment, following rotation of trigger member 120, one or more trigger lock members engage one or more complementary housing lock members to prevent further rotation of trigger member 120. This may be facilitated by proximal movement of trigger member 120 as a result of expansion of spring 150 following disengagement of trigger member 120 and mixing plunger sleeve 140. In one particular embodiment shown in FIG. 8C, the housing lock members are locking channels 116. Suitably, one or more trigger lock members 126 engage one or more complementary locking channels 116 within the housing 110 to prevent further rotation of trigger member 120. The locking channels 116 are configured to prevent axial rotation of the trigger member 120 and/or axial translation of the trigger member 120 in the locked state, Delivery plunger 130 is mounted to delivery plunger seal 160 which is axially, slidably movable in inner chamber 230 of inner barrel 110 of mixing device 200 to thereby deliver the mixed contents of the inner chamber 230. Delivery plunger 130 may be coupled to delivery plunger seal 160 by way of screw-threaded engagement of complementary screw threads 133 and 161, as shown in FIGS. 10A-10B, or by another form of contact engagement, as shown in FIG. 9E. At this stage automatic mixing syringe 10 is ready for delivery of its mixed substances. The rigid needle shield 15 is removed, the cannula 311 of retractable needle 310 is inserted into a recipient and delivery plunger 130 is depressed to deliver the mixed, fluid contents of inner chamber 230 to the recipient. Standard medical practices, such as manual agitation of the automatic mixing syringe 10 to further facilitate mixing of the substances and/or priming the syringe to remove any residual air prior to injection, may be performed prior to needle insertion and injection of fluid contents. The actuating device 100 with integrated plunger 130 described herein may be separately assembled from the remainder of the automatic mixing syringe 10. This may be desirable where, for example, a pharmaceutical company wishes to fill the syringe 10 with the drug substance(s) in their standard fill-finish lines, and seal and ship such filled components to a separate company for final assembly. Additionally, this may be desirable for shipping, transportation, or a number of other reasons. Furthermore, it may be desirable to have the actuating device 100 as a separable component from the mixing device 200 of the automatic mixing syringe 10 for safe and efficient disposal of the components separately (i.e., only the portions contaminated by use need to be disposed in a safety sharps container, while the remaining components may be disposed of separately).

In at least one embodiment of the present invention, the actuating device 100 is utilized with an automatic mixing syringe 10 having a needle retraction mechanism.

A preferred needle retraction mechanism comprises a needle assembly 300 comprising one or more biasing members that facilitate needle retraction. As shown in FIGS. 9A-E, in contrast to an embodiment to be described hereinafter, the needle assembly 300 comprises one or more biasing members 340 actuatable by delivery plunger 130, wherein there is no engagement between delivery plunger seal 160 and the retractable needle 310, release of a biasing member 340 in the needle assembly 300 causing retraction of the retractable needle 310. The embodiment shown in FIGS. 9A and 9B has a single biasing member 340 (e.g., a single spring) in the needle assembly 300; the embodiment shown in FIGS. 9C-E has a biasing member 340 comprising springs 342, 344.

Figure 9A:
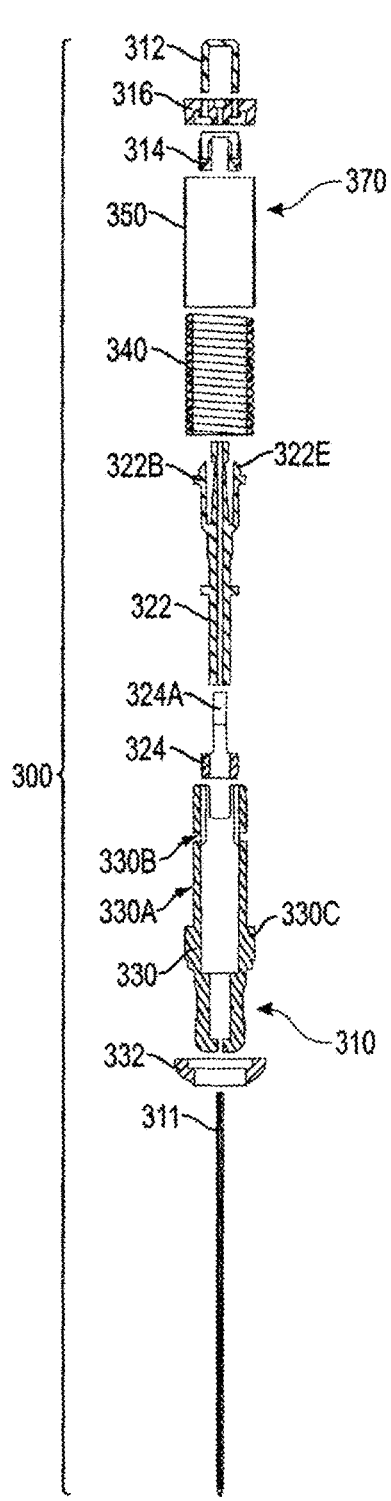
FIG. 9A shows an exploded sectional view of an embodiment of a needle retraction mechanism comprising a needle assembly having a biasing member comprising a single spring.
Figure 9B:
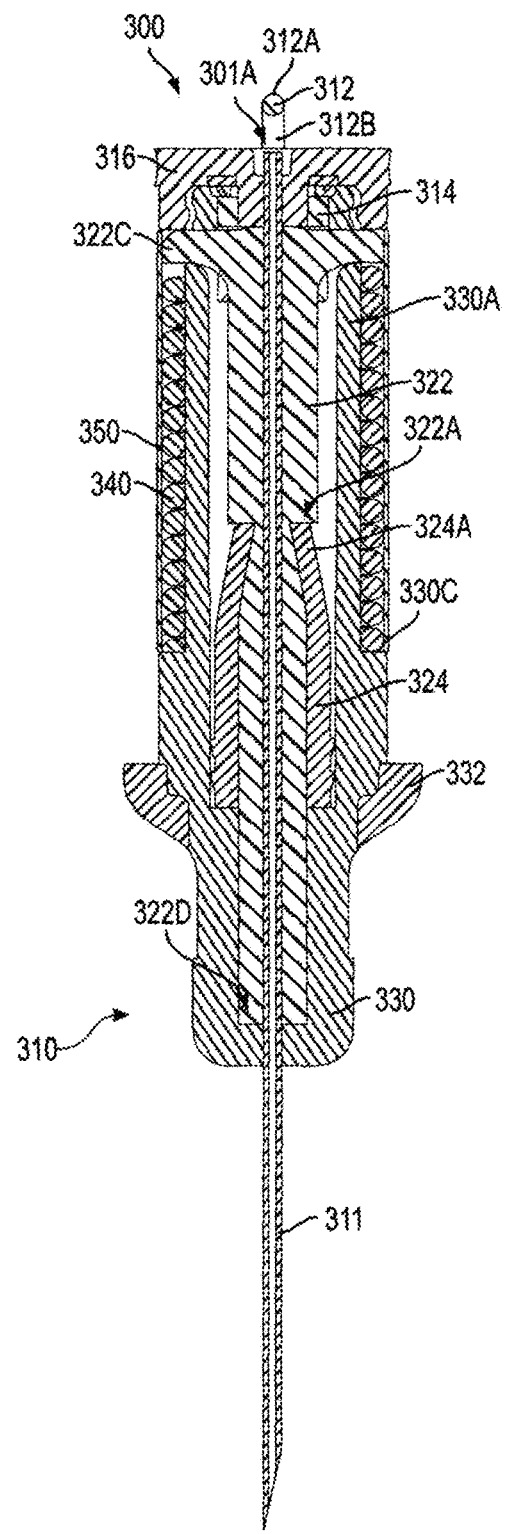
FIG. 9B shows a sectional view embodiment of a needle retraction mechanism comprising a needle assembly having a biasing member comprising a single spring.

FIGS. 9A and 9B show cross-sectional views according to one embodiment of the present invention. The needle assembly 300 includes retractable needle 310 comprising needle-over-mold ("NOM") 322, cannula 311, and, optionally, a needle blocking mechanism adapted to block the cannula 311 following retraction. In the illustrated embodiment, the needle blocking mechanism includes a clip 324. Clip 324 may initially slidably or removably engage NOM 322 such as, for example, at an engagement between clip arms 324A and NOM engagement surface 322A. Upon retraction of the cannula 301 and axial translation in the proximal direction of NOM 322, the clip arms 324A may flex inwards (i.e., towards the axis A) to contact NOM tip 322D in a needle blocking configuration. Such a needle blocking configuration prevents axial travel in the distal direction after retraction and retains the cannula 311 substantially within the barrel tip 330 and/or the barrel of the syringe 10.

Turning to FIG. 9A, the needle assembly 300 further includes an actuable locking arrangement disposed to maintain a biasing member 340 in an energized position until actuated by the actuator subassembly to retract the cannula 311. In the illustrated embodiment, the barrel tip 330 includes a spring guide 330A. In order to maintain the biasing member 340 in its initial energized position, the NOM 322 may initially be disposed in engagement with the barrel tip 330, sandwiching the energized biasing member 340 between one or more ledges 322C of the NOM 322 and an engagement surface 330C of the barrel tip 330. In one such embodiment of the actuable locking arrangement, the spring guide 330A of the barrel tip 330 may include one or more locking recesses or locking ledges 330B adapted to receive, for example, locking prongs 322B of NOM 122. As will be described further below, upon substantial completion of drug delivery through the fluid path, i.e., needle 310, the actuable locking arrangement may be actuated by the actuator subassembly to cause the locking prongs 322B to move inward and release from the locking recesses 330B of the barrel tip 330 to then permit the biasing member 340 to deenergize, exerting a force on the ledge(s) 322C of the NOM 322 to retract the needle 310.

The actuator subassembly 370 is disposed to actuate the actuable locking arrangement to permit the biasing member 340 to deenergize, retracting the needle 310. In the illustrated embodiment, the actuator subassembly 370 includes a needle seal 316, a push bar 312, and an actuator 314. In some embodiments, the push bar 312 is slidably disposed relative to the needle seal 316. In at least one embodiment, push bar 312 resides at least partially within a proximal end of the needle seal 316 and in contact with actuator 314 which resides distal to needle seal 316. Depression of the push bar in such a configuration is capable of contacting and depressing (or axially translating in the distal direction) the actuator 314. In at least an initial configuration, such as for needle insertion into the body of a user, the actuator subassembly 370 may reside proximal to and either in contact with or adjacent to the needle subassembly 320.

In at least one embodiment, push bar 312 includes a proximal contact surface 312A and one or more force transfer elements 312B that extend through corresponding throughways 316B in the needle seal 316. In assembly, the force transfer element 312B extending through the needle seal 316 engage the actuator 314 such that axial movement of the push bar 312 causes axial movement of the actuator 314. In this regard, the push bar 312 and the actuator 314 may be engaged and coupled together during the assembly process or the components may be disposed such assembly such that some axial movement of the push bar 312 is permitted before it engages and causes axial movement of the actuator 314. It is noted that the needle seal 316 may additionally include an opening 316A through which the proximal end of the cannula 311 extends to establish a path for drug delivery.

The actuator 314 includes one or more actuating surfaces 314A disposed to engage and actuate the actuable locking arrangement to actuate the needle retraction mechanism 311. To facilitate operation, in the illustrated embodiment, the actuating surfaces 314A are sloped and disposed to engage corresponding sloped surfaces 322E of the locking prongs 322B of the NOM 322. In this way, the axial movement of the actuator 314 causes the actuating surfaces 314A to slide along the sloped surfaces 322E of the locking prongs 322B to urge the locking prongs 322B radially inward, causing disengagement of the locking prongs 322B from the locking recesses 330B of the barrel tip 330. As a result, the biasing member 340 is permitted to at least partially deenergize, retracting the cannula 311.

In other words, in operation, the delivery plunger seal 160 (not shown) is caused to contact push bar 312. As a result, further depression of the plunger seal 160 during drug delivery causes axial translation of the push bar 312 in the distal direction at least partially through, or further through, needle seal 316. With the push bar 312 in contact with the actuator 314, axial translation of the push bar 312 results in axial translation of the actuator 314. Axial translation of the actuator 314 causes contact with, and flexion of, locking prongs 322B of NOM 122 to disengage the locking prongs 322B from the corresponding locking recesses 330B of the spring guide 330A.

Upon disengagement of the locking arrangement between the locking prongs 322B from the corresponding locking recesses 330B, biasing member 340 is permitted to expand in the proximal direction from its initial energized state to a reduced or deenergized state. This expansion in the proximal direction of the biasing member 340 pushes upon a ledge 322C of NOM 322 causing NOM 322 and cannula 311 to translate in the proximal direction to a retracted state. As described above, upon retraction of the needle 101 and axial translation in the proximal direction of NOM 322, the clip arms 324A may flex inwards (i.e., towards the axis A) to contact NOM tip 322D in a needle blocking configuration. Such a needle blocking configuration prevents axial travel in the distal direction after retraction and retains the needle 310 substantially within the barrel tip 330 and/or the barrel of the syringe. In at least one embodiment of the present invention, push bar 312 and actuator 314 are a unified or single component.

Figure 9C:
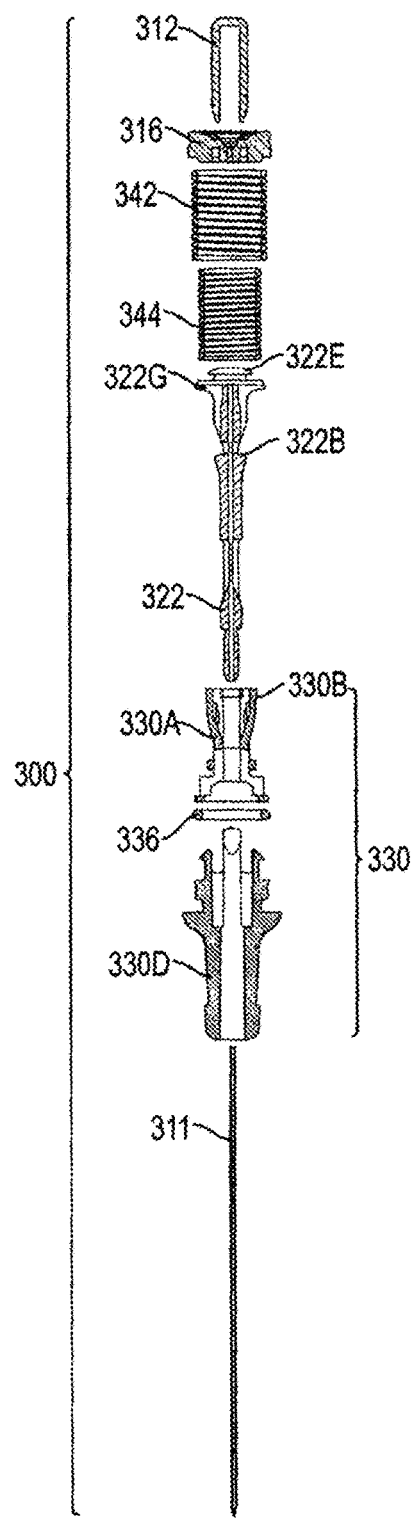
FIG. 9C shows an exploded sectional view of an embodiment of a needle retraction mechanism comprising a needle assembly having a biasing member comprising first and second springs.
Figure 9D:
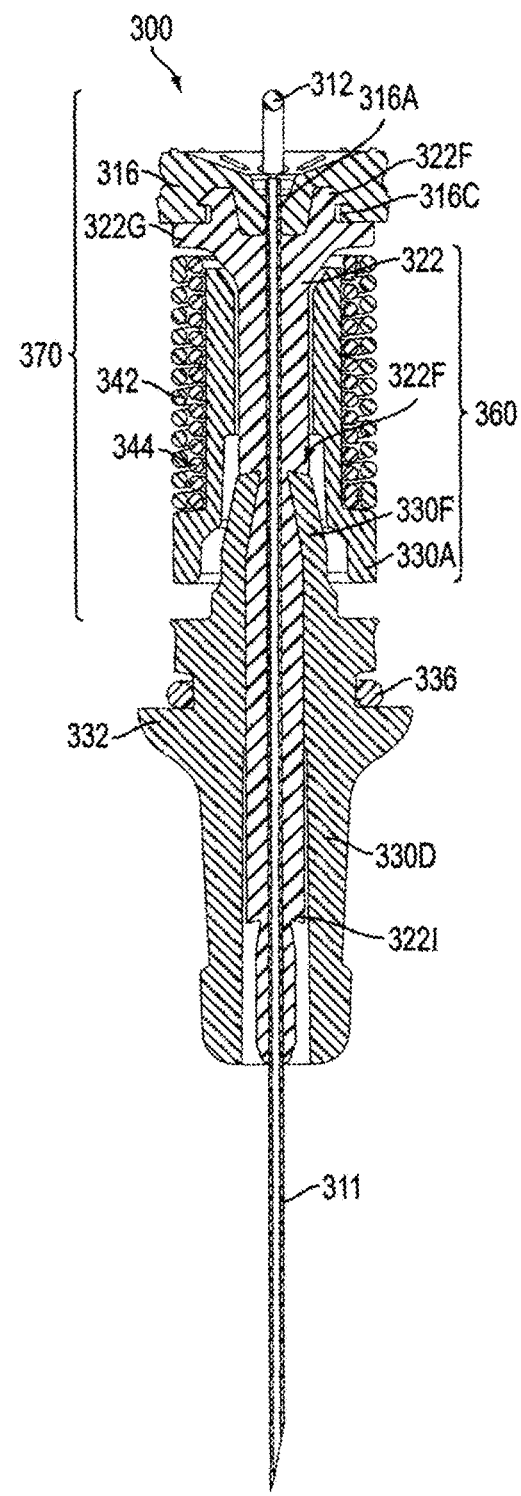
FIG. 9D shows a sectional view of an embodiment of a needle retraction mechanism comprising a needle assembly having a biasing member comprising first and second springs.
Figure 9E:
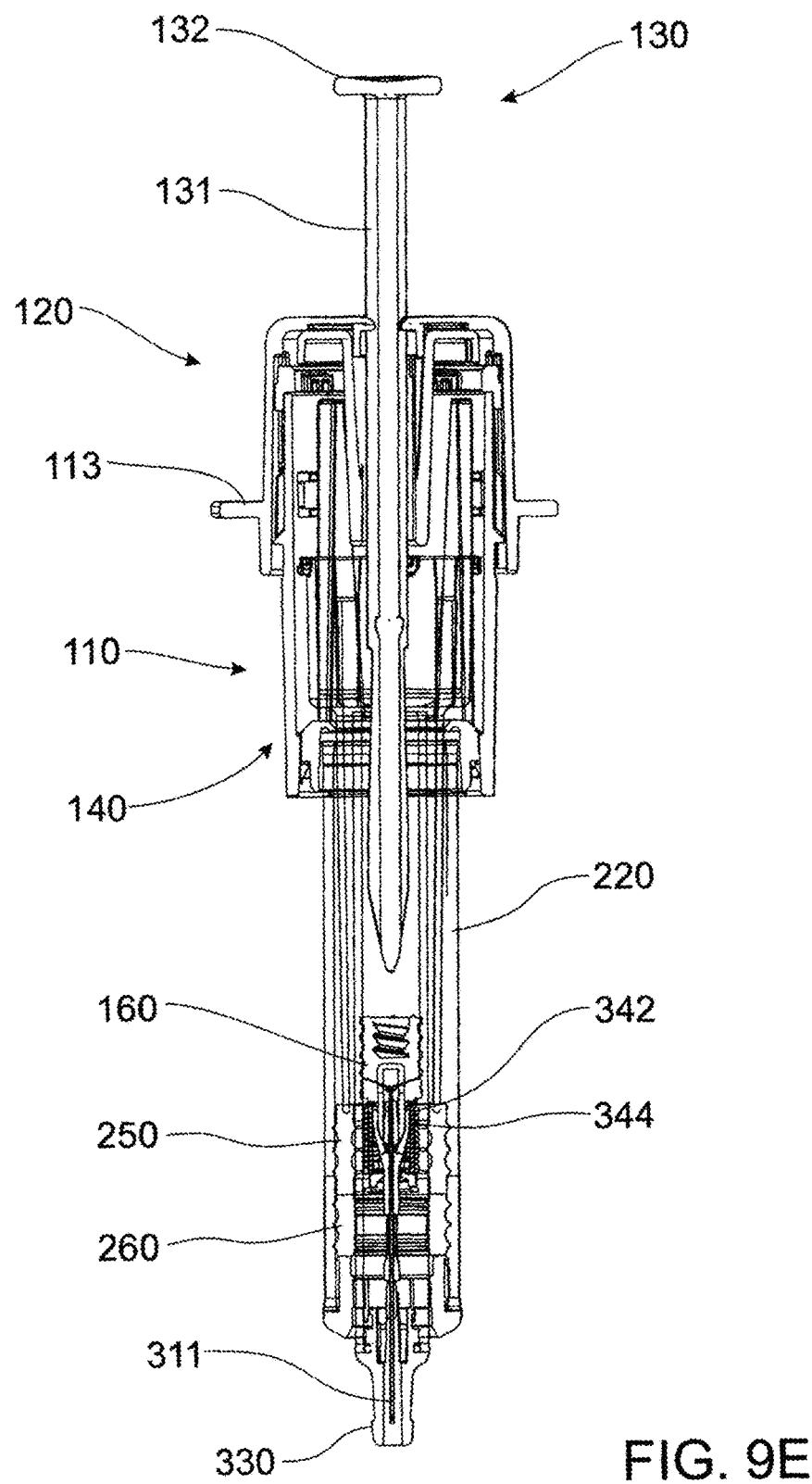
FIG. 9E shows a sectional view of the embodiment of FIGS. 9C and 9D in a retracted position.
Figure 10A:
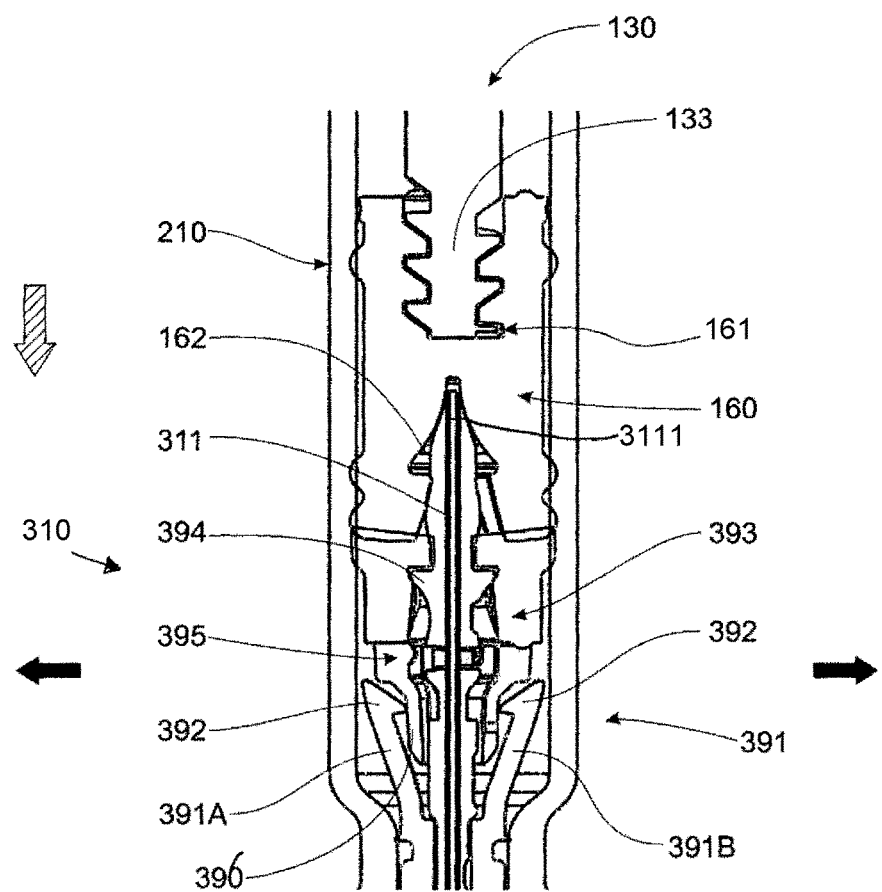
FIG. 10A shows an alternative embodiment of a needle assembly comprising a retractable needle engageable by a delivery plunger seal.
Figure 10B:
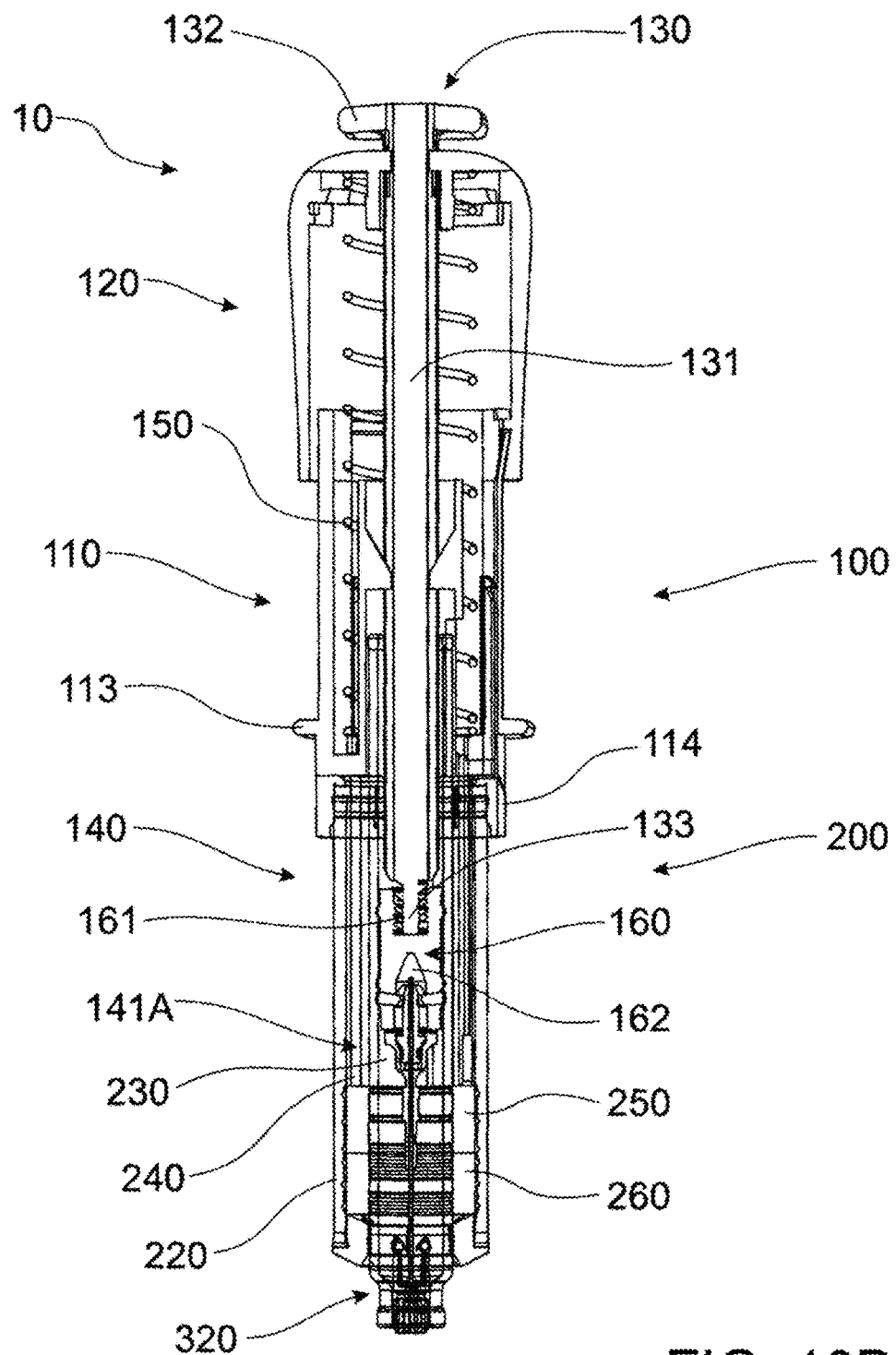
FIG. 10B shows a sectional view of the embodiment of FIG. 10A, where the biasing member of the actuating device facilitates retraction of the retractable needle when engaged by the delivery plunger seal.

Turning to FIGS. 9C-E, there is shown another embodiment of needle assembly 300 that includes a barrel tip 330 and a needle subassembly 320, a needle retraction subassembly 360, and an actuator subassembly 370. The needle subassembly 320 includes a cannula 311 and a needle-overmold (NOM) 322. The actuator subassembly 370 includes a needle seal 316, and a push bar 312. The needle subassembly 320 is engaged with the needle seal 316 with a proximal end of the cannula 311 extending through an opening 316A in the needle seal 316. The NOM 322 may be securely coupled to the needle seal 316 in any appropriate manner. For example, in the illustrated embodiment, the NOM 322 includes a plurality of flanges, a first of such flanges 322F engaging an internal flange 316C of the needle seal 316, and a second of said flanges 322G being disposed along a lower surface of the needle seal 316. Further features of the NOM will be described below with regard to the relationship of the needle retraction subassembly 360 and the actuator subassembly 370.

The push bar 312 includes a proximal contact surface 312A and at least one depending force transfer element 312B. Here, a pair of force transfer elements 312B extends through throughways in the needle seal 316. In assembly, the proximal contact surface 312A is disposed proximal the needle seal 316. In contrast to the embodiment in FIGS. 9A and 9B, however, the force transfer element 312B of the push bar 312 includes actuating surfaces 312C, here, angled surfaces. In other words, this embodiment does not include a separate actuator. Rather, the push bar 312 and actuator are a unitary component.

The needle retraction subassembly 360 includes at least one biasing member 340 and an actuable locking arrangement. In this embodiment, the biasing member 340 includes a pair of springs 342, 344. While the springs 342, 344 are disposed in parallel and the support structure is such that they move toward a deenergized position simultaneously, the springs 342, 344 could alternately be disposed and supported such that they move toward a deenergized position in series. Whether disposed in series or in parallel, the inclusion of two or more springs may provide certain advantages in reducing the size of the overall package of the barrel adapter 350. It will be appreciated, however, that supporting the springs in parallel 342, 344 may further enhance these advantages.

In this embodiment, the barrel tip 330 includes multiple components. That is, the spring guide 330A is formed separately from the tip portion 330D, the spring guide 330A and the tip portion 330D being coupled together during assembly. The biasing members 340, or springs 342, 344, may be received around the spring guide 330A. Inserting the assembly of the needle subassembly 320 and the actuator subassembly 370 into the spring guide 330A, the needle subassembly 320 and the spring guide 330A may be coupled together to retain the biasing members 340 in an energized position between engagement surface 330C and ledge 322C. In contrast to the first embodiment, in this embodiment, the spring guide 330A includes at least one locking prong 330B, here, a pair of locking prongs 330B, and the NOM 322 includes a locking ledge 322B. It will thus be appreciated that when the push bar 312 is contacted by the plunger seal 160 (not shown) at the end of administration of medication, the actuating surfaces 312C of the push bar 312 push the locking prongs 330B of the spring guide 330A outward, disengaging them from the locking ledge 322B of the NOM 322. As a result, the biasing members 340 are permitted to release energy to retract the needle subassembly 320 into the barrel, as shown in FIG. 9E. In such embodiments, the trigger member 120 does not need to move substantially in the proximal direction to enable retraction of needle subassembly 320 because the push bar 312 activates retraction of the needle subassembly directly into the inner barrel 210.

Figure 10C:
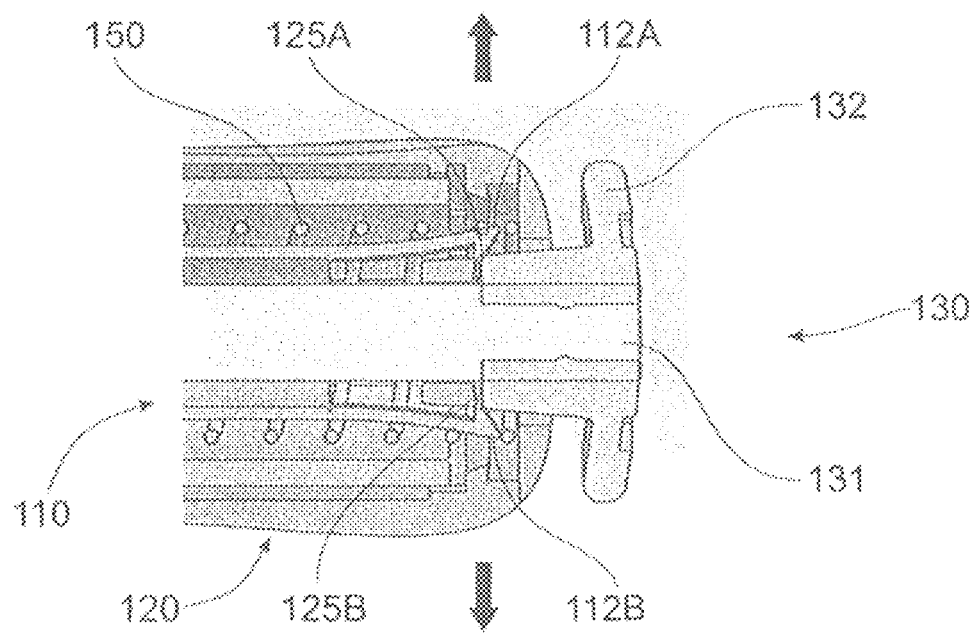
FIG. 10C shows a sectional view of the embodiment of FIG. 10A, where the delivery plunger engages the housing to release the biasing member of the actuating device to facilitate retraction of the retractable needle when engaged by the delivery plunger seal.

In an alternative embodiment, the retractable needle 310 is retracted by engagement with the delivery plunger seal 160, whereby biasing member 150 of actuation device 100 facilitates retraction of the retractable needle 310. In the particular embodiment shown in FIGS. 10A and B, delivery plunger 130 comprises shaft 131 and seal-engaging member 133, which in this embodiment is a screw threaded projection, which engages a complementary, screw-threaded recess 161 of delivery plunger seal 160. In this embodiment where the retractable needle 310 is retracted by engagement with the delivery plunger seal 160, the delivery plunger seal 160 further comprises needle-engaging portion or recess 162. In at least one embodiment, needle assembly 300 comprises retractable needle 310 comprising cannula 311 and needle body 394, retainer 391 having arms 391A, B and hook-ends 392A, B, needle seal 393 and ejector 395 having ejector ring 396. The needle retraction mechanism shown in FIGS. 10A and B is essentially similar to that described in WO2011/075760. During delivery of fluid contents, delivery plunger 130 and coupled delivery plunger seal 160 moves axially through inner chamber 230 in the direction of the hatched arrow in FIGS. 10A-C. Delivery plunger seal 160 bears against needle seal 314, which in turn bears against ejector 395. Further to this, ejector ring 396 moves hook-ends 392A, B of arms 391A, B of retainer 391 radially outwardly in the direction of the solid arrows in FIG. 10A, thereby disengaging needle body 394 from retainer 390 to release retractable needle 310 for subsequent retraction. At this point, needle-engaging portion or recess 162 of delivery plunger seal 160 has engaged retractable needle body 394 and received fluid end 3111 of cannula 311. This effectively couples retractable needle 310 to delivery plunger seal 160 and delivery plunger 130.

Figure 10D:
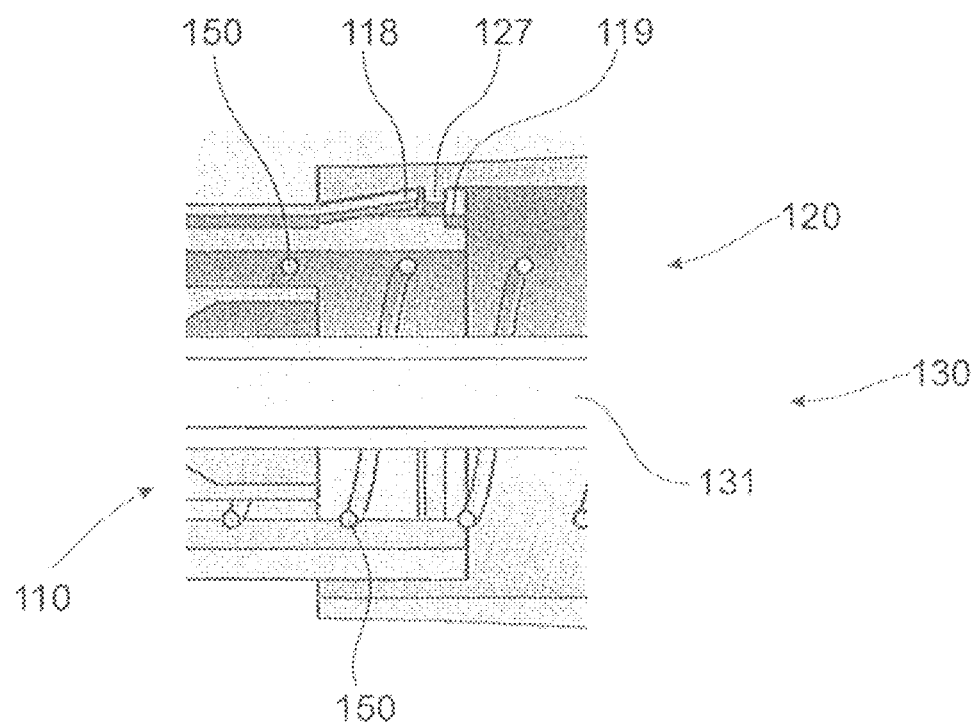
FIG. 10D shows a sectional view of an embodiment of the actuating device where the trigger member and delivery plunger are in locking engagement after mixing and delivery of the mixed contents of the syringe.

As shown in FIG. 10B, in order for retractable needle 310 to retract at the end of delivery of fluid contents, biasing member 150 must de-energize from its partially or reduced energized state. As hereinbefore described, the biasing member 150 is initially utilized to depress the sleeve 140 (i.e., axially translate in the distal direction) to facilitate the mixing of the first and second substances. Upon suitable activation of the retraction mechanism, such as by capture of the retractable needle 310 as described herein and in WO2011/075760, the biasing member 150 can also be utilized to retract the retractable needle 310 (axially translate in the proximal direction). Initially, the trigger member 120 is held in releasable engagement by housing prongs 112A, B engaging with corresponding retention slots 125A, B of the trigger member 120. Disengagement of these components is facilitated by the proximal end of the plunger 130 and/or button 131 at the end of drug delivery. As plunger 130 and/or button 131 are substantially fully depressed (i.e., axially translated in the distal direction) to inject fluid from inner chamber 230, one or both may contact the housing prongs 112A, B. Through this contact, housing prongs 112A, B are moved radially and out of engagement with corresponding retention slots 125A, B of the trigger member 120 in the direction of the solid arrows. This disengagement allows partially compressed biasing member 150 to further decompress and push against trigger member 120 to thereby push against and retract plunger 130. Delivery plunger seal 160 coupled to retractable needle 310 is axially translated in the proximal direction by decompression of the biasing member 150, thereby retracting retractable needle 310 as shown in FIG. 10B. Trigger member 120 may be caused to translate axially in the proximal direction and retract the delivery plunger 130, delivery plunger seal 160 and retractable needle 310 connected thereto. Retainer 390, ejector 395 and needle seal 393 remain at the distal end of inner chamber 230, as shown in FIG. 10B. As shown in FIG. 10D, at the end of retraction of the trigger member 120, plunger 130, delivery plunger seal 160 and retractable needle 310, the trigger member 120 and delivery plunger 130 (and associated components connected thereto) may be locked out by one or more locking ledges 127 of the trigger member 120 and one or more respective snap arms 118 of the housing 110. In addition to retraction of the needle into the barrel(s) of the mixing device, this lockout prevents reuse or tampering of the automatic mixing syringe 10 and makes it safe to dispose. It is also shown in FIG. 10D that the interaction between the one or more locking ledges 127 of the trigger member 120 and one or more respective tabs 119 of the housing 110 limits the axial travel of the trigger member relative to the housing 110, thereby preventing any unintended uncoupling of the trigger member 120 and housing 110.

Figure 11A:
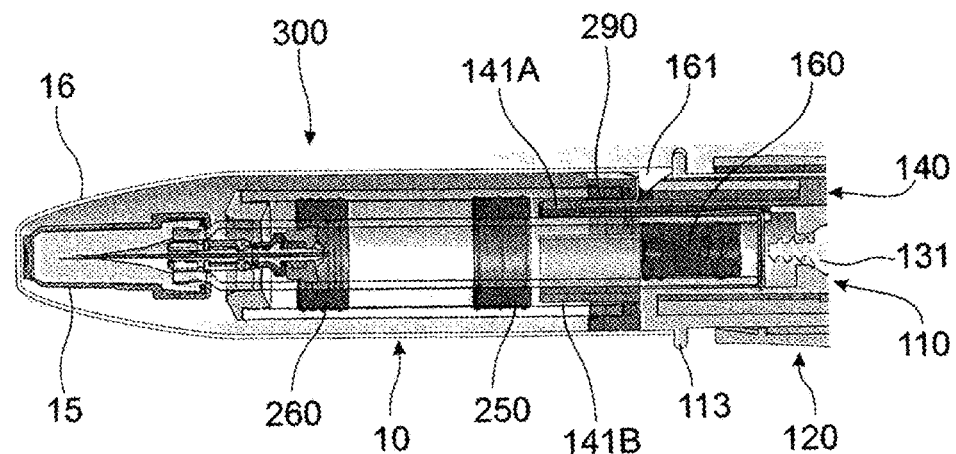
FIGS. 11A-11B show an embodiment of the automatic mixing syringe further comprising an optional cover mounted thereto.
Figure 11B:
Figure 11B:
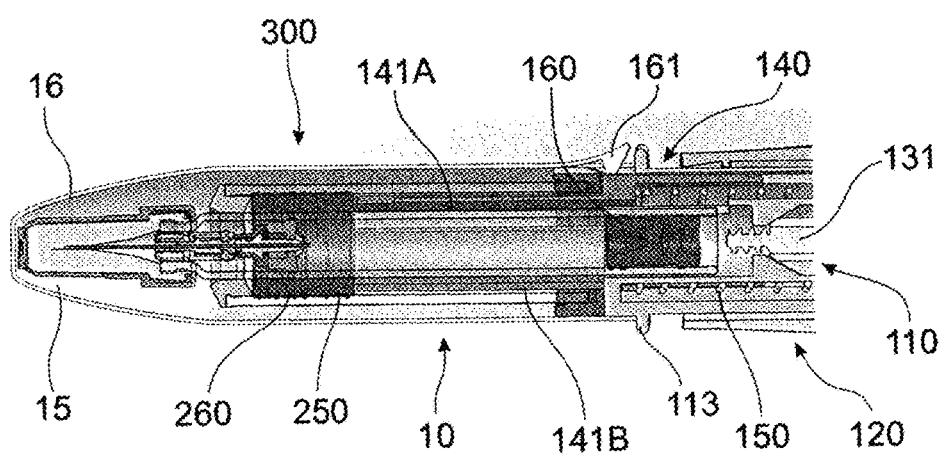
Figures 12A, 12B:
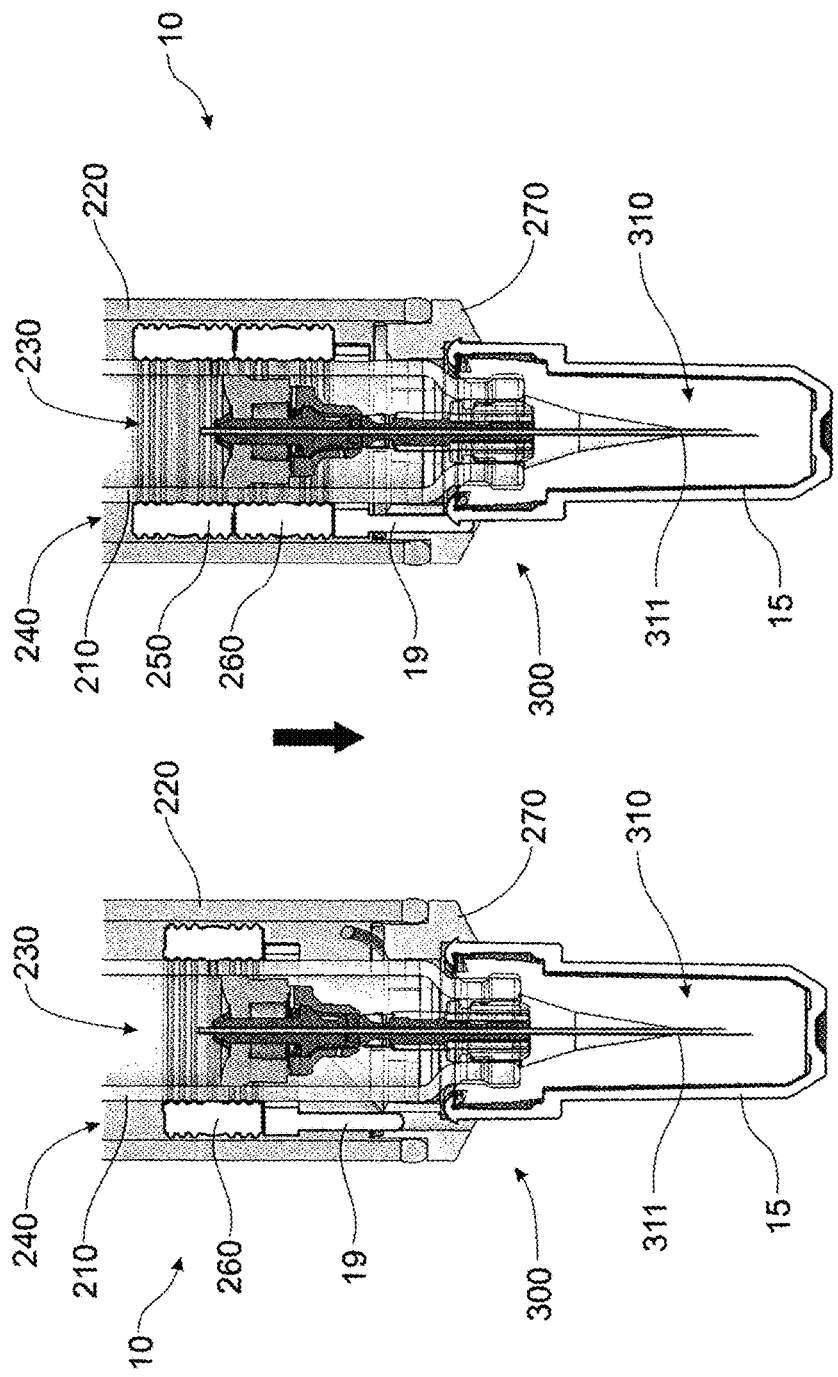
FIGS. 12A-12B show an embodiment of the automatic mixing syringe further comprising an alternative embodiment of a needle shield component of an optional cover.

The automatic mixing syringes 10 of the present invention may have optional covers which are automatically disengaged and removal only upon successful operation of the mixing stages of the syringe. FIGS. 11A and 11B show one embodiment having a distal cover 16. As shown in FIGS. 11A and 11B, the distal cover 16 comprises one or more flexible barb arms 161 that can be disengaged from housing 110, allowing removal of distal cover 16, only upon successful completion of the mixing stage as a result of axial travel of mixing plunger 140 in the direction shown by the solid arrow. Such covers may integrate or function with a safety cap and/or a rigid needle shield to prevent inadvertent operation of the mixing syringe. FIGS. 12A and 12B show another embodiment of the mixing syringe having a stand-alone collar-type safety cap 17. Upon displacement of the distal seal 260 in the direction of the solid arrow during mixing of substances, the distal seal 260 bears against and disengages collar-type safety cap 17 to thereby allow removal of needle shield 15 at the end of mixing. In the embodiments disclosed herein, it is possible to configure the safety caps 16, 17 such that they are removable only after successful completion of the mixing stages, thereby permitting removal of the rigid needle shield 15 and exposing the cannula 311 for injection.

Figure 13:
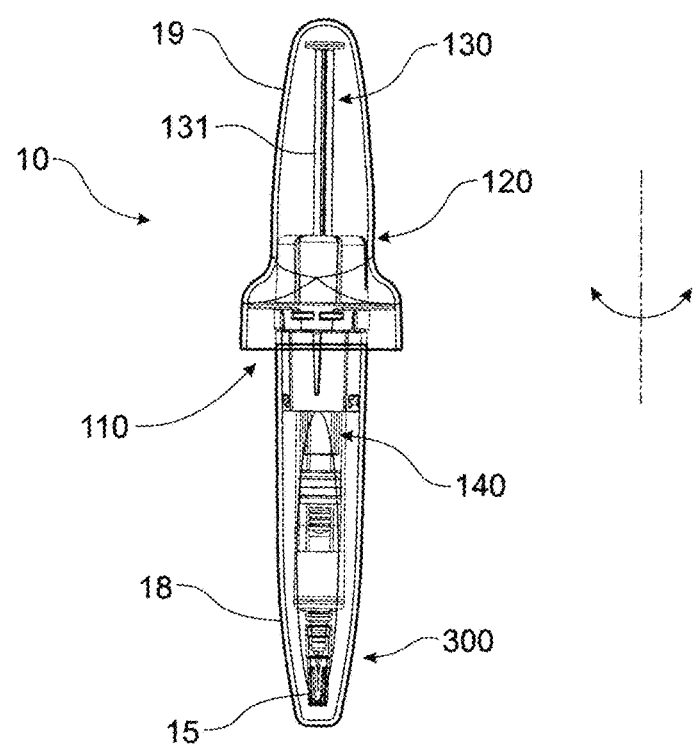
FIG. 13 shows an embodiment of the automatic mixing syringe having proximal and distal covers.

In at least one embodiment shown in FIG. 13, the automatic mixing syringe 10 may comprise distal cover 18 and proximal cover 19. Such covers may take a range of known shapes and configurations, such as conical, cylindrical, rectangular, and the like. This embodiment may be particularly useful or applicable for rapid or emergency mixing and delivery of substances that regulate blood glucose such as lyophilized insulin or glucagon. In this embodiment, proximal cover 19 is coupled to trigger member 120 so that rotation or twisting of proximal cover 19 co-ordinately rotates trigger member 120 to activate mixing of substances as hereinbefore described. Distal cover 18 is coupled to rigid needle shield 15 so that subsequent removal of distal cover 18 can "automatically" remove, in at least one embodiment, the rigid needle shield 15 to thereby expose cannula 311 for use. Proximal cover 19 can then be removed and delivery plunger 130 operated to enable delivery of the mixed substances to a recipient by injection. This embodiment provides a very rapid, safe and simply-operated mixing and delivery system for use during an emergency, such as typically encountered by diabetics. In such an embodiment, the covers 18, 19 serve as both general packaging for, and functional aspects of, the automatic mixing syringe 10.

It will be appreciated from the foregoing that the actuating device, automatic mixing device and syringe disclosed herein provide an efficient and easily-operated automatic system for mixing multiple substances prior to delivery by the syringe. There is no need to rotate or otherwise orient the inner and outer barrels prior to use to open or align fluid pathways, unlike in many prior art mixing devices such as those previously described. The positioning of the distal seal relative to the vents in the outer barrel and the apertures in the inner barrel keeps the contents of the mixing device sterile while providing adequate venting, which is in contrast to many prior art mixing devices such as previously described.

Assembly and/or manufacturing of actuating device, automatic mixing device, retractable syringe, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. To add the one or more apertures to the inner barrel, known drilling or boring methodologies such as mechanical or laser drilling may be employed. Furthermore, known sterilization processes may be employed at one or more of the manufacturing or assembly stages to ensure the sterility of the final product.

In yet another aspect, the invention provides a method of assembling a syringe comprising an automatic mixing device including the step of removably mounting an actuating device to a mixing device of the syringe so that a sleeve of the actuating device is operable to depress a mixing plunger seal of the mixing device. In one embodiment, the method includes the step of releasably connecting or coupling a housing of the actuating device to an outer barrel of the mixing device. In one embodiment, the method includes the step of releasably connecting or coupling a housing of the actuating device to an outer barrel of the mixing device. In one embodiment, the method further includes, prior to step (i), affixing a vent cap comprising the one or more vents to a portion of the inner barrel that is located distally of the one or more apertures. Preferably, the distal end of the outer barrel is connected to the vent cap. In a further embodiment, the method further includes the step of attaching a sealing membrane to the proximal end of the inner barrel of the mixing device prior to attachment of the actuating device to the mixing device. In a preferred embodiment, the sealing membrane is attached such that it is at least partially pierced or penetrable by operation of the delivery plunger. In another embodiment, the sealing membrane is attached in a manner such that it is removed automatically by operation of the sleeve of the actuating device, i.e., axial translation of the sleeve in the distal direction. Preferably, the method further includes the step of inserting a needle assembly into the inner chamber located distally of the one or more apertures.

In a further aspect, the invention provides a method of manufacturing a syringe including the step of removably mounting an actuating device to a mixing device mounted to a syringe.

In a still further aspect, the invention provides a method of operating a syringe comprising an automatic mixing device, said method including the steps of:
  (i) operating an actuating device of the automatic mixing device to facilitate mixing a plurality of substances, wherein operation of the actuating device removes a removable membrane from attachment to the mixing device;
  (ii) connecting a plunger of the actuating device to a delivery plunger seal of the mixing device;
  (iii) operating the plunger to deliver the substances mixed at step (i) to a recipient.

In one embodiment, the method includes the step of unlocking the plunger prior to step (iii). Unlocking the plunger may occur between steps (i) and (ii) in at least one embodiment or between steps (ii) and (iii) in other embodiments of the invention.

In an alternative embodiment, a method of operating a syringe comprising an automatic mixing device includes the steps of:
  (iv) operating an actuating device of the automatic mixing device to facilitate mixing a plurality of substances;
  (v) operating a plunger of the actuating device to pierce a sealing membrane to engage a delivery plunger seal of the mixing device;
  (vi) operating the plunger to deliver the substances mixed at step (i) to a recipient.

The method may further include the step of unlocking the plunger prior to step (iii). Unlocking the plunger may occur between steps (i) and (ii) in at least one embodiment or between steps (ii) and (iii) in other embodiments of the invention.

In at least one embodiment, the method of operating a syringe comprising an automatic mixing device further includes: (iv) activating a needle retraction mechanism to retract the needle into the syringe. Preferably, the activation of the needle retraction mechanism occurs after substantially all of the substances are delivered to the recipient.

As discussed above, a number of aspects of the present invention may be facilitated by separate components. Alternatively, one or more components of the present invention may be a unified component and/or the functions of such one or more components may be accomplished by a unified component. For example, the trigger member, and several other components, can be single unified components or made up of smaller sub-components (e.g., the interior aspects of the trigger member, particularly the components at the proximal interior end of the trigger member, may be sub-components that snap together or otherwise function as one component). It is readily understood by one having ordinary skill in the art that such components may be unified components or comprised of separate sub-components, such as for manufacturability, while remaining within the breadth and scope of the presently claimed invention.

A number of known filling processes and equipment may be utilized to achieve the filling steps of the syringe manufacturing process. In one embodiment, the second fluid substance may be filled as a liquid substance and lyophilized in situ using certain barrel heat transfer equipment. The needle assembly, delivery plunger, and other components described in these manufacturing and assembly processes may be as described above or may be a number of similar components which achieve the same functionality as these components.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. An actuating device mountable to an automatic mixing syringe, said syringe including an inner barrel, an outer barrel, an outer chamber between the inner barrel and the outer barrel, a delivery plunger seal disposed in the inner barrel, and at least one mixing plunger seal disposed in the outer chamber between the inner barrel and the outer barrel, the actuating device comprising a housing connectable to the syringe, a rotatable trigger member, a biasing member, a delivery plunger disposed to bear against the delivery plunger seal of the syringe, and a mixing plunger releasably engaged with the trigger member in an initially locked state, the mixing plunger being disposed to bear against the at least one mixing plunger seal of the syringe, wherein said trigger member is operable to initiate said biasing member to facilitate depression of said mixing plunger when engaged with said at least one mixing plunger seal.

2. The actuating device of claim 1, wherein rotation of the trigger member disengages the mixing plunger from the trigger member to initiate said biasing member to facilitate depression of said mixing plunger when engaged with the at least one mixing plunger seal to thereby mix a plurality of substances in said syringe.

3. The actuating device of claim 1, wherein the mixing plunger comprises at least one prong and the trigger member comprises at least one slot member, and wherein in the initially locked state the at least one prong initially engages the at least one slot member and is rotatable out of engagement with the at least one slot member to initiate said biasing member to facilitate depression of said mixing plunger when engaged with said at least one mixing plunger seal to thereby mix a plurality of substances in said syringe.

4. The actuating device of claim 1, wherein the housing comprises at least one abutment and the delivery plunger comprises at least one channel, wherein in the initially locked state, the at least one abutment is not aligned with the at least one channel to thereby prevent axial travel of the delivery plunger and further wherein rotation of the trigger member can rotate the delivery plunger to align the at least one abutment of the housing with the at least one channel in the delivery plunger to thereby permit axial travel of the delivery plunger.

5. The actuating device of claim 1, wherein the trigger member comprises at least one trigger lock member and the housing comprises at least one housing lock member and wherein following rotation of the trigger member, the at least one trigger lock member can engage the at least one housing lock member to prevent further rotation of the trigger member.

6. The actuating device of claim 1, wherein the biasing member is initially retained in an energized state between the trigger member and the mixing plunger.

7. The actuating device of claim 6, wherein upon disengagement of the mixing plunger from the trigger member, the biasing member expands from its energized state to translate the mixing plunger axially and axial translation of the mixing plunger bears upon and axially translates the at least one mixing plunger seal of the syringe.

8. The actuating device of claim 1, wherein the biasing member is initially retained within an interior chamber of the trigger member.

9. An automatic mixing syringe comprising an inner barrel, an outer barrel, an outer chamber between the inner barrel and the outer barrel, a delivery plunger seal disposed in the inner barrel, at least one mixing plunger seal disposed in the outer chamber between the inner barrel and the outer barrel, and an actuating device according to claim 1 mounted thereto, wherein the outer barrel and the inner barrel are in a substantially coaxial or concentric relationship.

10. The automatic mixing syringe of claim 9, wherein the at least one mixing plunger seal is axially moveable within the outer chamber.

11. The automatic mixing syringe of claim 9, wherein the at least one mixing plunger seal includes a proximal seal and a distal seal that are moveable within the outer chamber.

12. The automatic mixing syringe of claim 9, wherein the inner barrel comprises at least one fluid path through which a first mixing substance in the outer chamber can enter an inner chamber in the inner barrel to thereby form a mixture with a second mixing substance.

13. The automatic mixing syringe of claim 9, which comprises a sealing membrane that maintains sterility of the automatic mixing syringe prior to operation.

14. The automatic mixing syringe of claim 9 further comprising a needle assembly.

15. The automatic mixing syringe of claim 14, wherein the needle assembly comprises a retractable needle engageable by the delivery plunger seal.

16. The automatic mixing syringe of claim 14, wherein the needle assembly comprises at least one biasing member operable to retract the retractable needle.

17. The automatic mixing syringe of claim 14, wherein a needle-engaging portion of the delivery plunger seal is configured to engage a retractable needle body.

18. The automatic mixing syringe of claim 17, wherein the biasing member of the actuating device is operable to activate retraction of the retractable needle body when engaged by the needle-engaging portion of the delivery plunger seal.

19. The automatic mixing syringe of claim 14, further comprising a removable proximal cover and a removable distal cover wherein the removable proximal cover is operable to rotate the trigger member to initiate said biasing member to facilitate depression of said mixing plunger when engaged with said at least one mixing plunger seal.

20. The automatic mixing syringe of claim 19, wherein the removable distal cover is operable to remove a needle shield covering a needle.

* * * * *